United States Patent [19]
Bridges et al.

[11] Patent Number: 5,866,792
[45] Date of Patent: Feb. 2, 1999

[54] PLANT-DERIVED ENZYME AND DNA SEQUENCES AND USES THEREOF

[75] Inventors: Ian George Bridges, Hampshire; Simon William Jonathan Bright, Buckinghamshire; Andrew James Greenland, Berkshire; David Charles Holt, Berkshire; Ian Jepson, Berkshire; Wolfgang Walter Schuch, Berkshire, all of England

[73] Assignee: Zeneca Limited, London, England

[21] Appl. No.: 664,855

[22] Filed: Jun. 17, 1996

Related U.S. Application Data

[62] Division of Ser. No. 170,294, filed as PCT/GB92/01187, Jul. 1, 1992, Pat. No. 5,589,614.

[30] Foreign Application Priority Data

Jul. 2, 1991 [GB] United Kingdom .................... 9114259

[51] Int. Cl.$^6$ ................ A01H 5/00; A01H 5/10; C12N 9/10; C12N 15/29; C12N 15/52; C12N 15/85
[52] U.S. Cl. .............. 800/205; 435/172.3; 435/193; 435/320.1; 435/419; 536/23.2; 536/23.6; 800/250; 47/58
[58] Field of Search ................... 536/23.2, 23.6; 435/172.3, 193, 419, 320.1; 800/205, DIG. 9, DIG. 43, DIG. 52, DIG. 56, 250; 47/58, DIG. 61

[56] References Cited

U.S. PATENT DOCUMENTS 5,073,677   12/1991   Helmer et al. .......................... 800/205

FOREIGN PATENT DOCUMENTS 256223   2/1988   European Pat. Off. .
9008826   8/1990   WIPO .

OTHER PUBLICATIONS

Biochemistry, vol., No. 5, 1983, pp. 1068–1072, Mozer, T. J., et al, "Purification and characterization of corn glutathione S–transferase" see the whole document.
WOA 9,008830, Aug. 9, 1990, see the whole document.
Plant Molecular Biology, vol. 6, No. 4, 1986, pp. 203–211, Shah et al, Structural analysis of glutathione–S–transferase involved in herbicide detoxification see the whole document.
WO, A, 9 008 830, Aug. 9, 1990, see p. 1–p. 7, see p. 18–p. 25, figures 1,2.
Biotechnology vol. 3, Jul. 1985, pp. 629–635, Fraley, et al: "The SEV system: a new disarmed Ti plasmid vector system for plant transformation", see p. 632, right column, paragraph 1.
Gene, vol. 76, 1989, pp. 153–160, Wosnick et al: "Total chemical synthesis and expression in *Eschericha coli* of a maze glutathione–transferase (GST) gene" see the whole document.
Nucleic Acids Research, vol. 14, No. 18, 1986, pp. 7227–7235 Moore et al: "Cloning and expression of a cDNA encoding a maize glutathione–S–transferase gene in E. coli" see page 7227 introduction para. 2.
Physiol. Plant. vol. 77, No. 3, 1989, pp. 465–471 Timmerman, "Molecular characterization of com glutathione S–transferase isozymes involved in herbicide detoxification".
Nucleic Acids Research, vol. 16, No. 2, 1988, pp. 425–438, Grove et al; "Characterization and heterospecific expression of cDNA clones of genes in the maize GSH S–transferase multigene family" see the whole document.
J. Cell. Biochem. Suppl., Meeting Apr. 10–16, 1992, vol. 16F, 1992, p. 232, Greenland et al: "Cloning and analysis of a cDNA clone encoding a glutathione–S–transferase subunit from maize which is induced by treatment with herbicide safeners", See Abstract Y412.

*Primary Examiner*—Douglas W. Robinson
*Assistant Examiner*—Amy J. Nelson
*Attorney, Agent, or Firm*—Melissa A. Shaw; Marian T. Thomson

[57] ABSTRACT

The chemically-inducible 27 kD subunit of the enzyme glutathione-S-transferase, isoform II (GST-II-27) and sequences encoding it are provided. In particular, a genomic DNA sequence encoding the gene promoter for the GST-II-27 subunit is provided. Then linked to an exogenous gene and introduced into a plant by transformation, and GST-II-27 promoter provides a means for the external regulation of expression of that exogenous gene. Transformation with DNA encoding glutathione-S-transferase polypeptides produces herbicide resistance transgenic plants.

17 Claims, 21 Drawing Sheets

```
  1 CCAGCTGCTG ATCTTGATCC TGCACCCCGA GCCGTACACA AGAGCTAGTC
    GGTCGACGAC TAGAACTAGG ACGTGGGGCT CGGCATGTGT TCTCGATCAG

51 GGTAGAACTT GCAGGAGCGG AGCAGAACTA AGTGCAGAGA ACAGGACATA
    CCATCTTGAA CGTCCTCGCC TCGTCTTGAT TCACGTCTCT TGTCCTGTAT

101 TGGCTACGCC GGCGGTGAAG GTTTACGGGT GGGCTATCTC GCCGTTCGTA
    ACCGATGCGG CCGCCACTTC CAAATGCCCA CCCGATAGAG CGGCAAGCAT

151 TCGCGGGCTC TGCTGGCCCT GGAGGAGGCC GGCGTCGACT ACGAGCTCGT
    AGCGCCCGAG ACGACCGGGA CCTCCTCCGG CCGCAGCTGA TGCTCGAGCA

201 CCCCATGAGC CGCCAGGACG GCGACCACCG CCGCCCCGAG CACCTCGCCA
    GGGGTACTCG GCGGTCCTGC CGCTGGTGGC GGCGGGGCTC GTGGAGCGGT

251 GGAACCCTTT CGGGAAGGTG CCGGTGCTCG AGGATGGCGA CCTCACGCTC
    CCTTGGGAAA GCCCTTCCAC GGCCACGAGC TCCTACCGCT GGAGTGCGAG

301 TTCGAATCAC GTGCGATCGC GAGGCATGTT CTCCGGAAGC ACAAGCCGGA
    AAGCTTAGTG CACGCTAGCG CTCCGTACAA GAGGCCTTCG TGTTCGGCCT

351 GCTGCTGGGC GGCGGCAGGC TGGAGCAGAC GGCGATGGTG GACGTGTGGC
    CGACGACCCG CCGCCGTCCG ACCTCGTCTG CCGCTACCAC CTGCACACCG

401 TGGAGGTGGA GGCCCACCAG CTGAGCCCCG CGGCGATCGC CATCGTGGTG
    ACCTCCACCT CCGGGTGGTC GACTCGGGGC GCCGCTAGCG GTAGCACCAC
```

FIG. 2A

```
401  TGGAGGTGGA GGCCCACCAG CTGAGCCCGC CGGCGATCGC CATCGTGGTG
     ACCTCCACCT CCGGGTGGTC GACTCGGGCG GCCGCTAGCG GTAGCACCAC

451  GAGTGCGTGT TCGCGCCGTT CCTGGGCCGC GAGCGCAACC AGGCGGTGGT
     CTCACGCACA AGCGCGGCAA GGACCCGGCG CTCGCGTTGG TCCGCCACCA

501  GGACGAGAAC GTGGAGAAGC TCAAGAAGGT GCTGGAGGTG TACGAGGCGC
     CCTGCTCTTG CACCTCTTCG AGTTCTTCCA CGACCTCCAC ATGCTCCGCG

551  GGCTGGCCAC GTGCACGTAC CTCGCCGGCG ACTTCCTCAG CCTCGCCGAC
     CCGACCGGTG CACGTGCATG GAGCGGCCGC TGAAGGAGTC GGAGCGGCTG

601  CTCAGCCCCT TCACCATCAT GCACTGCCTC ATGGCCACCG AGTACGCCGC
     GAGTCGGGGA AGTGGTAGTA CGTGACGGAG TACCGGGTGGC TCATGCGGCG

651  TCTCGTCCAT GCGCTCCCGC ACGTCAGCGC CTGGTGGCAG GGCCTCCGCCG
     AGAGCAGGTA CGCGAGGGCG TGCAGTCGCG GACCACCGTC CCGGAGCGGC

701  CGGCGCCCGC GGCCAACAAG GTGGCGCAGT TCATGCCGGT CGGCGCCGGA
     GCCGCGGGCG CCGGTTGTTC CACCGCGTCA AGTACGGCCA GCCGCGGCCT

751  GCGCCCAAGG AACAGGAGTG ACGATGAAGC GATCGAAGCG ACTTGTGTTG
     CGCGGGTTCC TTGTCCTCAC TGCTACTTCG CTAGCTTCGC TGAACACAAC
```

FIG. 2B

```
801  TTGTGCTTGA  TTAGTTAATT  GGAAACCTTC  TCACTCATCT  AGTCCATCAT
     AACACGAACT  AATCAATTAA  CCTTTGGAAG  AGTGAGTAGA  TCAGGTAGTA

851  GGTGCCTGCT  TTTCTTTATA  CTATTTGTCT  TAATTTTGCT  GCTTTCTCCA
     CCACGGACGA  AAAGAAATAT  GATAAACAGA  ATTAAAACGA  CGAAAGAGGT

901  CGGAATAATA  GTAGAGATTT  GGAAATGTAA  TGTATTTATC  AAAAAAAAAA
     GCCTTATTAT  CATCTCTAAA  CCTTTACATT  ACATAAATAG  TTTTTTTTTT

951  AAAA
     TTTT
```

FIG. 2C

```
GSTII    MATPAVKVYGWAISPFVSRALLALEEAGVDYELVPMSRQDGDHRRPEHLA          50
GSTIPEP  MA--PMKLYGAVMSWNLTRCATALEEAGSDYEIVPINFATAEHKSPEHLV          48
GST3PEP  MA--PLKLYGMPLSPNVVRVATVLNEKGLDFEIVPVDLTTGAHKQPDFLA          48
         **  . *.** .*         .*.*.* . *.**.   .  .*.**:*

GSTII    RNPFGKVPVLEDGDLTLFESRAIARHVLRKHKPE----LLGGGRLEQTAMV         97
GSTIPEP  RNPFGQVPALQDGDLYLFESRAICKYAARKNKPE----LLREGNLEEAAMV         95
GST3PEP  LNPFGQIPALVDGDEVLFESRAINRYIASKYASEGTDLLPAT--ASAAKL          96
         ****.:* : ***  ******  :  : :  .*      *       .:

GSTII    DVWLEVEAHQLSPPAIAIVVECVFAPFLGRERNQAVVDENVEKLKKVLEV         147
GSTIPEP  DVWIEVEANQYTAALNPILFQVLISPMLGGTTDQKVVDENLEKLKKVLEV         145
GST3PEP  EVWLEVESHHFHPNASPLVFQLLVRPLLGGAPDAAVVEKHAEQLAKVLDV         146
         :**:***:.:   .      ::  *:**      .**:. :: *.**:*

GSTII    YEARLATCTYLAGDFLSLADLSPFTIMHCLMAT--EYAALVHALPHVSAW         195
GSTIPEP  YEARLTKCKYLAGDFLSLADLSPFTLCLFAT--PYASVLDAYPHVKAW           193
GST3PEP  YEAHLARNKYLAGEFTLADANH--ALLPALTSARPPRPGCVAARPHVKAW         195
         ***:**   *****:*  **: .    . ::   * :        ***.**

GSTII    WQGLAARPAANKVAQFMPVGAGAPKEQEX                           224
GSTIPEP  WSGLMERPSVQKVAALM-------KPSA                            214
GST3PEP  WEAIAARPAFQKTVAAIPLP--PPPSSSA                           222
         *  : :***  :.    :           .
```

FIG. 3

```
3539  tccctcccgtcgaccaaatacacttggtcttctctagcacctcttcttctctccaagactc caa
   7                                                                  CAAT Box 3600  tccctcccgtcgaccaaatacacttggtcttctctagcacctcttcttctctccaagactccaa
   7 tcccccaaccaccagaaccagcgccagctctaacgtcacctctgatttctctctcctctct
   7

3661  attgctagctgctttatt tata agtagcagctgcagcaggcaggagctgcacacccatcc
   7                      TATA Box                                   TSP
                                                                     ↑
      attgctagctgctttattattaagtagcagctgcagcaggcaggagctgcacacccatcc
                   PRIMER P1

3722  aattCCAGCTGCTGCTTGATCTTGATCCTTGCACCCCGAGCCCGTACACAAGAGCTAGTCGGTAGAA
   7      ||||||||||||||||||||||||||||||||||||||||||||||||||||||||||||
          CCAGCTGCTGCTTGATCTTGATCCTTGCACCCCGAGCCTGTACACAAGAGCTAGTCGGTAGAA
                                                    PRIMER GST PRIM aattCCAGCTGCTGCTGATCTTGATCCTTGCACCCCGAGCCCGTACACAAGAGCTAGTCGGTAGAA 3783  CTTGCAGGAGCGGAGCGGAGCAGAACTAAGTGCAGAGAACAGGACATATGGCTACGCCGCGGGTGA
  64  ||||||||||||||||||||||||||||||||||||||||||||||||||||||||||||||||
      CTTGCAGGAGCGGAGCGGAGCAGAACTAAGTGCAGAGAACAGGACATATGGCTACGCCGCGGGTGA
                                                  TRANSLATION START

CTTGCAGGAGCGGAGCGGAGCAGAACTAAGTGCAGAGAACAGGACATATGGCTACGCCGCGGGTGA
```

FIG. 4

```
gaattccaaatatatgatgattgttgtcctagtgcagaagaactaaatatactagcgaaaaaaaccttc
ctagtcatgtaagtgtatggcatatagaaaataaacatctcaagactccaaactagtcatagctttta
gtcacaacttcaaacactcatgccaacaagatcatgatttttttttgcctaagacaaaactagaat
gagaaaagaactaactcatcatacatattagtatgcatgacacatatgatACTAT
ATCACACAGGCCTTCAGTTTCTAGAACAAGTGCAGATCGAtgtgtgggtatgcatgtctaatatttact
aggttggatatgcatgggcgttcattcagaatcagttcacacagtttcacgcacttctgtttacaaaac
atggatttcattgctctgtactgcctgctaaggatcaactcgcgtaaggatcaactcgcgtactgatgcactcggtctcaatctagatcaatctaggtgcatccctcctt
gtcaagcaaacttaacaatttgataaaaaaatgcagctttatatgtgaacccataactaacttaatatgga
caggaaactgatgtgcaacaacAAAAACTAAAATAGGAaaacacacaagttccaaatgtatataattg
tcaccatagtgcaaaagaaccaaatatactgcagagaaaactcctagtcatgtaagtAAAATGGACATAT
AGAAATAAAACATCTCAAGACTCCAATAACAGGCTCAAGCTAACTAGTCATGGCTTTAAACCTTCATGAT
GCAAACTAGTCACAACTTTAAACATTTCATGCCAACAAGATCATGGATGTGTTTTTTTTCCTAGGGAA
AAGCTAGAATGAGAAAAGACCTAACTCAGCATACATATCAGGATAGTATCAGGATATCAGACACGTATATGATA
CTATATCACGCAGCCGTTCAATTTCTAGAACAAATGCAGATTGATCTGTGAATATGCATGTCTCATATTT
TACTAGGTTGGATGGAATCCCGTGAATCCCGTGATAAAAAAAATGCAACCAACAGTTAACCAGAAGTGAAAATAGAAAC
tcaaattcaataatcactctcgttgataaaaaaatgcaaccaacagttaaccagaagtgaaaatagaaac
tatttgaatcagatcactccgttattcacacacagtaacaagaacagtacagcttataaaagcagtaggaac
attgttaaccatcaatttcaagtacacagtaacaagaacagtacagctagaattgagcatgtgagtATT
GTTGATACCTCGTTGAGCTCTCTCGCCGCGGCTTTCTGCGAAAACACGCGCGGTACGCCAAGAGAGCCAGCTCAGGATCCACC
ccgaaagcttgggcgtaggtgttgtctatcggcgaaacacgcgcgcgtacgccaagacagcgcggccat
```

FIG. 7A

```
ctccatccaggcacggtgcgcccgcttttcgccgctctcgctgagtcacggcgcggcgtccagcaggtag
ttgagcgcttccgcgcggcacgaatcgctgcgtgcggccggatctcGGTTGGTCGAGTTGGTCAGCGTCGGT
GTCGAATGCCGGGACGTCgaccaggaagaagttgccgtcgtgggtggggacggaaggcgtcaggattg
tcgcaaggggcagagcccagctGCCggGGCTACCTCGTCGACCCTCGcACGGCCGGCgCAAAGCT
GcTGCGGGAcgTGCccgCCTGGGCCCGCCTTCTCGGTGAAGTGGtCCtcgaagggacgagctcgtgggg
tcaaaccacccCataGctcGAGTcACcGAAgAAGGCGACGAGGACGAGCCCGTcGcGGTGGCCgcgGTGT
ACCTCCTCGTCGGTGAggctGACGCTGTAGATATGGCCAGGCCACCACGGATGGACTTCACCTTGG
CCCAGACCATGTCGCCGAACCGGGGCCCGCCGTTCGCGCGTTGTGAGGGGAACCGAAAACCTAGATTTGGATGCAGGTTCG
GGCGCCTCCAGCGGCGGACATCCTCGGACACTCCTGTGGAGgGGGTGGCCTGGgAGGGTGGCCTGGGGATCGGTGGAGGAGGACATTGTTG
ATTGGTCTGGGCTTGGGTTCCGGagGGGTGGCCTGGGATCGGTGGAGGAGGACATTGTTG
GTAATTTTATTATTTATATAGtgTAAAATAGTATTTTATCAAGTTTATATTCACGTTTTTGCTCTCATATCATATCTACTAT
ATGTAGTATAAAGtgTAAAATAGTATTTTATCAAGTTTATATTCACGTTTTTGCTCTCATATCATATCTACTAT
GTGGAGTTGTTTTGGCGCTACATAATTCACTTTGTGTAATCTACACTATAAAATAGTGTTTTACACGGTATGTTGT
CACATTCTCTATTTAAATTCACTTTGTGTAATCTACACTATAAAATAGTGTTTTACACGGTATGTTGT
ACACAGCCTTATCGTGcGCGAcgGAGTTGGATAGAGATGGTGAACAGCTGGATAGATGATTTATAGG
CGATTGGTAGATGTGATTTGATAGTGGTTATGTGATAGGAGCGATTAGTGTGAGACATTGTAAATAATTAGG
TTGATGTGATCCGAGGATGGCTAGGTAGATGGCTAGATATGATTTAATGGATGGTTTGGTGGACTAAGTTATGTGAA
CATTATAATATGTTTAAATTTCTAAGAAATTGTTTGTTAAATATTCGTTTGCTTCTACAATTATATGTTTT
ATCCAAAGAGAGGTTTGGGTTTGTTTACACAAATAAAATATTCGTTTGCTTCTACAATTATATGTTTT
TATTTACATGAAAACTATATTTTTATTCATCTACTCACCCAGCACACAGAAATTCTGGTTGAGTAGATGAA
```

FIG. 7B

```
AAAAACTACAACAAACTCTTCCTGAAAGTGTCGGTGTGAAGCCCGAGAAATCCTTTCATTCGGTGACG
GAGCCCCTTGCTCTGCTGCTCAGTGCACTCCGTTCGCCTCGCCTGCCACTACAAGCGACGGCCGACGAC
TCGCAAGTATCGGTAGGCATTTAAAACTGAAAACCAAATCTAAACCCGAATAGACCAAATTGTTGGTTT
ATTCGGGTTTTTGGGTTCGGATTCGGTTTCTAAATATGCTATATTTAGGGTATAGGTTCGGGTTCAGTT
TCTAACCTTTAAAACCTGAATAGACGAATAACCCGAAATATAAAAAATCTCTTAATATGTGATGATATTA
TTATATGATTTATGAACTTATTAACCGAAAATAATGATACCATCCTAACGATAGTATATATCTATGTA
TGCTATTTTATAGTCACTTGTTGTAATAATAGTACTTCCAATTAATAATCAGTGTATATATTTAACA
AAAGATACTAGCCCTCTCACTATTGAGTATATTCGGTGCACCGAATAGACCGAAATTGTAAGTC
TATTCAGTTCGGTTCGTTCCTAAATTATTTAAAAATTTTGTTCTCATATTTCAGAATCCGAAATTTCATA
AATCCAAATAGACCGAAACCAAATTaCGCTAATAGACCGAATAACTAGCGTACTCgCAAGTCGCACCCCAC
TAGCCTGCTGCGTGCGTAAGCGAGGACGTCACGCGTTCTCCCTCCCGTCGACCAAATACACTTGGTCTTC
TAGCACCTTCCTCTCCCAAGaCTCCAAGTAGTAGCAGCCTGCAGCCCgGCCagCTcTAACGTCACCT
CTGATTTCTCTCTCCTTCTATTGCTAGCCTGCTGCTGATCTTGATCCTGCACCCCGAGCGCTGCA
CACACCCATCCAATTCCAGCTGGGAgCAGAACTAAGTGCAGAGAACAGGACATATG
```

| translation start point

FIG. 7C

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 954 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( B ) STRAIN: GSTII-27 - FIGURE 2

( x i ) SEQUENCE DESCRIPTION: SEQ ID NO:1:

| | | | | | |
|---|---|---|---|---|---|
| CCAGCTGCTG | ATCTTGATCC | TGCACCCCGA | GCCGTACACA | AGAGCTAGTC | GGTAGAACTT | 60 |
| GCAGGAGCGG | AGCAGAACTA | AGTGCAGAGA | ACAGGACATA | TGGCTACGCC | GGCGGTGAAG | 120 |
| GTTTACGGGT | GGGCTATCTC | GCCGTTCGTA | TCGCGGGCTC | TGCTGGCCCT | GGAGGAGGCC | 180 |
| GGCGTCGACT | ACGAGCTCGT | CCCCATGAGC | CGCCAGGACG | GCGACCACCG | CCGCCCGGAG | 240 |
| CACCTCGCCA | GGAACCCTTT | CGGGAAGGTG | CCGGTGCTCG | AGGATGGCGA | CCTCACGCTC | 300 |
| TTCGAATCAC | GTGCGATCGC | GAGGCATGTT | CTCCGGAAGC | ACAAGCCGGA | GCTGCTGGGC | 360 |
| GGCGGCAGGC | TGGAGCAGAC | GGCGATGGTG | GACGTGTGGC | TGGAGGTGGA | GGCCCACCAG | 420 |
| CTGAGCCCGC | CGGCGATCGC | CATCGTGGTG | GAGTGCGTGT | TCGCGCCGTT | CCTGGGCCGC | 480 |
| GAGCGCAACC | AGGCGGTGGT | GGACGAGAAC | GTGGAGAAGC | TCAAGAAGGT | GCTGGAGGTG | 540 |
| TACGAGGCGC | GGCTGGCCAC | GTGCACGTAC | CTCGCCGGCG | ACTTCCTCAG | CCTCGCCGAC | 600 |
| CTCAGCCCCT | TCACCATCAT | GCACTGCCTC | ATGGCCACCG | AGTACGCCGC | TCTCGTCCAT | 660 |
| GCGCTCCCGC | ACGTCAGCGC | CTGGTGGCAG | GGCCTCGCCG | CGCGCCCGGC | GGCCAACAAG | 720 |
| GTGGCGCAGT | TCATGCCGGT | CGGCGCCGGA | GCGCCCAAGG | AACAGGAGTG | ACGATGAAGC | 780 |
| GATCGAAGCG | ACTTGTGTTG | TTGTGCTTGA | TTAGTTAATT | GGAAACCTTC | TCACTCATCT | 840 |
| AGTCCATCAT | GGTGCCTGCT | TTTCTTTATA | CTATTTGTCT | TAATTTGCT | GCTTTCTCCA | 900 |
| CGGAATAATA | GTAGAGATTT | GGAAATGTAA | TGTATTTATC | AAAAAAAAAA | AAAA | 954 |

( 2 ) INFORMATION FOR SEQ ID NO:2:

( i ) SEQUENCE CHARACTERISTICS:
        ( A ) LENGTH: 224 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: GSTII FIGURE 4

( x i ) SEQUENCE DESCRIPTION: SEQ ID NO:2:

```
Met  Ala  Thr  Pro  Ala  Val  Lys  Val  Tyr  Gly  Trp  Ala  Ile  Ser  Pro  Phe
  1                 5                        10                       15

Val  Ser  Arg  Ala  Leu  Leu  Ala  Leu  Glu  Glu  Ala  Gly  Val  Asp  Tyr  Glu
               20                       25                       30

Leu  Val  Pro  Met  Ser  Arg  Gln  Asp  Gly  Asp  His  Arg  Arg  Pro  Glu  His
                35                       40                       45

Leu  Ala  Arg  Asn  Pro  Phe  Gly  Lys  Val  Pro  Val  Leu  Glu  Asp  Gly  Asp
          50                       55                       60

Leu  Thr  Leu  Phe  Glu  Ser  Arg  Ala  Ile  Ala  Arg  His  Val  Leu  Arg  Lys
 65                      70                       75                       80

His  Lys  Pro  Glu  Leu  Leu  Gly  Gly  Gly  Arg  Leu  Glu  Gln  Thr  Ala  Met
                    85                       90                       95

Val  Asp  Val  Trp  Leu  Glu  Val  Glu  Ala  His  Gln  Leu  Ser  Pro  Pro  Ala
               100                      105                      110

Ile  Ala  Ile  Val  Val  Glu  Cys  Val  Phe  Ala  Pro  Phe  Leu  Gly  Arg  Glu
              115                      120                      125

Arg  Asn  Gln  Ala  Val  Val  Asp  Glu  Asn  Val  Glu  Lys  Leu  Lys  Lys  Val
              130                      135                      140

Leu  Glu  Val  Tyr  Glu  Ala  Arg  Leu  Ala  Thr  Cys  Thr  Tyr  Leu  Ala  Gly
145                      150                      155                      160
```

-continued

```
         Asp  Phe  Leu  Ser  Leu  Ala  Asp  Leu  Ser  Pro  Phe  Thr  Ile  Met  His  Cys
                        165                      170                      175

Leu  Met  Ala  Thr  Glu  Tyr  Ala  Ala  Leu  Val  His  Ala  Leu  Pro  His  Val
                        180                      185                      190

Ser  Ala  Trp  Trp  Gln  Gly  Leu  Ala  Ala  Arg  Pro  Ala  Ala  Asn  Lys  Val
                        195                      200                      205

Ala  Gln  Phe  Met  Pro  Val  Gly  Ala  Gly  Ala  Pro  Lys  Glu  Gln  Glu  Xaa
                        210                      215                      220
```

( 2 ) INFORMATION FOR SEQ ID NO:3:

( i ) SEQUENCE CHARACTERISTICS:
        ( A ) LENGTH: 214 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: GSTI. FIGURE 4

( x i ) SEQUENCE DESCRIPTION: SEQ ID NO:3:

```
         Met  Ala  Pro  Met  Lys  Leu  Tyr  Gly  Ala  Val  Met  Ser  Trp  Asn  Leu  Thr
         1              5                        10                       15

Arg  Cys  Ala  Thr  Ala  Leu  Glu  Glu  Ala  Gly  Ser  Asp  Tyr  Glu  Ile  Val
                        20                       25                       30

Pro  Ile  Asn  Phe  Ala  Thr  Ala  Glu  His  Lys  Ser  Pro  Glu  His  Leu  Val
                        35                       40                       45

Arg  Asn  Pro  Phe  Gly  Gln  Val  Pro  Ala  Leu  Gln  Asp  Gly  Asp  Leu  Tyr
                   50                       55                       60

Leu  Phe  Glu  Ser  Arg  Ala  Ile  Cys  Lys  Tyr  Ala  Ala  Arg  Lys  Asn  Lys
         65                       70                       75                       80

Pro  Glu  Leu  Leu  Arg  Glu  Gly  Asn  Leu  Glu  Glu  Ala  Ala  Met  Val  Asp
                             85                       90                       95

Val  Trp  Ile  Glu  Val  Glu  Ala  Asn  Gln  Tyr  Thr  Ala  Ala  Leu  Asn  Pro
                        100                      105                      110

Ile  Leu  Phe  Gln  Val  Leu  Ile  Ser  Pro  Met  Leu  Gly  Gly  Thr  Thr  Asp
                        115                      120                      125

Gln  Lys  Val  Val  Asp  Glu  Asn  Leu  Glu  Lys  Leu  Lys  Lys  Val  Leu  Glu
                   130                      135                      140

Val  Tyr  Glu  Ala  Arg  Leu  Thr  Lys  Cys  Lys  Tyr  Leu  Ala  Gly  Asp  Phe
         145                      150                      155                      160

Leu  Ser  Leu  Ala  Asp  Leu  Asn  His  Val  Ser  Val  Thr  Leu  Cys  Leu  Phe
                        165                      170                      175

Ala  Thr  Pro  Tyr  Ala  Ser  Val  Leu  Asp  Ala  Tyr  Pro  His  Val  Lys  Ala
                        180                      185                      190

Trp  Trp  Ser  Gly  Leu  Met  Glu  Arg  Pro  Ser  Val  Gln  Lys  Val  Ala  Ala
                        195                      200                      205

Leu  Met  Lys  Pro  Ser  Ala
                        210
```

( 2 ) INFORMATION FOR SEQ ID NO:4:

( i ) SEQUENCE CHARACTERISTICS:
        ( A ) LENGTH: 222 amino acids
        ( B ) TYPE: amino acid
        ( C ) STRANDEDNESS: single
        ( D ) TOPOLOGY: linear ( i i ) MOLECULE TYPE: peptide (vi) ORIGINAL SOURCE:
(A) ORGANISM: GSTIII FIGURE 4

(xi) SEQUENCE DESCRIPTION: SEQ ID NO:4:

| Met | Ala | Pro | Leu | Lys | Leu | Tyr | Gly | Met | Pro | Leu | Ser | Pro | Asn | Val | Val |
|---|---|---|---|---|---|---|---|---|---|---|---|---|---|---|---|
| 1 | | | | 5 | | | | | 10 | | | | | | 15 |

| Arg | Val | Ala | Thr | Val | Leu | Asn | Glu | Lys | Gly | Leu | Asp | Phe | Glu | Ile | Val |
|---|---|---|---|---|---|---|---|---|---|---|---|---|---|---|---|
| | | | 20 | | | | | 25 | | | | | 30 | | |

| Pro | Val | Asp | Leu | Thr | Thr | Gly | Ala | His | Lys | Gln | Pro | Asp | Phe | Leu | Ala |
|---|---|---|---|---|---|---|---|---|---|---|---|---|---|---|---|
| | | 35 | | | | | 40 | | | | | 45 | | | |

| Leu | Asn | Pro | Phe | Gly | Gln | Ile | Pro | Ala | Leu | Val | Asp | Gly | Asp | Glu | Val |
|---|---|---|---|---|---|---|---|---|---|---|---|---|---|---|---|
| | 50 | | | | | 55 | | | | | 60 | | | | |

| Leu | Phe | Glu | Ser | Arg | Ala | Ile | Asn | Arg | Tyr | Ile | Ala | Ser | Lys | Tyr | Ala |
|---|---|---|---|---|---|---|---|---|---|---|---|---|---|---|---|
| 65 | | | | | 70 | | | | | 75 | | | | | 80 |

| Ser | Glu | Gly | Thr | Asp | Leu | Leu | Pro | Ala | Thr | Ala | Ser | Ala | Ala | Lys | Leu |
|---|---|---|---|---|---|---|---|---|---|---|---|---|---|---|---|
| | | | | 85 | | | | | 90 | | | | | 95 | |

| Glu | Val | Trp | Leu | Glu | Val | Glu | Ser | His | His | Phe | His | Pro | Asn | Ala | Ser |
|---|---|---|---|---|---|---|---|---|---|---|---|---|---|---|---|
| | | | 100 | | | | | 105 | | | | | 110 | | |

| Pro | Leu | Val | Phe | Gln | Leu | Leu | Val | Arg | Pro | Leu | Leu | Gly | Gly | Ala | Pro |
|---|---|---|---|---|---|---|---|---|---|---|---|---|---|---|---|
| | | 115 | | | | | 120 | | | | | 125 | | | |

| Asp | Ala | Ala | Val | Val | Glu | Lys | His | Ala | Glu | Gln | Leu | Ala | Lys | Val | Leu |
|---|---|---|---|---|---|---|---|---|---|---|---|---|---|---|---|
| | 130 | | | | | 135 | | | | | 140 | | | | |

| Asp | Val | Tyr | Glu | Ala | His | Leu | Ala | Arg | Asn | Lys | Tyr | Leu | Ala | Gly | Asp |
|---|---|---|---|---|---|---|---|---|---|---|---|---|---|---|---|
| 145 | | | | | 150 | | | | | 155 | | | | | 160 |

| Glu | Phe | Thr | Leu | Ala | Asp | Ala | Asn | His | Ala | Leu | Leu | Pro | Ala | Leu | Thr |
|---|---|---|---|---|---|---|---|---|---|---|---|---|---|---|---|
| | | | | 165 | | | | | 170 | | | | | 175 | |

| Ser | Ala | Arg | Pro | Pro | Arg | Pro | Gly | Cys | Val | Ala | Ala | Arg | Pro | His | Val |
|---|---|---|---|---|---|---|---|---|---|---|---|---|---|---|---|
| | | | 180 | | | | | 185 | | | | | 190 | | |

| Lys | Ala | Trp | Trp | Glu | Ala | Ile | Ala | Ala | Arg | Pro | Ala | Phe | Gln | Lys | Thr |
|---|---|---|---|---|---|---|---|---|---|---|---|---|---|---|---|
| | | 195 | | | | | 200 | | | | | 205 | | | |

| Val | Ala | Ala | Ile | Pro | Leu | Pro | Pro | Pro | Pro | Ser | Ser | Ser | Ala |
|---|---|---|---|---|---|---|---|---|---|---|---|---|---|
| | 210 | | | | | 215 | | | | | 220 | | |

(2) INFORMATION FOR SEQ ID NO:5:

(i) SEQUENCE CHARACTERISTICS:
(A) LENGTH: 305 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: PRIMER EXTENSION MAP FIGURE 5

(xi) SEQUENCE DESCRIPTION: SEQ ID NO:5:

```
TCCCTCCCGT  CGACCAAATA  CACTTGGTCT  TCTAGCACCT  TCTTCCTCTC  CAAGACTCCA      60
ATCCCCCAAC  CACCAGAACC  AGCGCCAGCT  CTAACGTCAC  CTCTGATTTC  TCTCTCCTCT     120
CTATTGCTAG  CTGCTTTATT  ATAAGTAGCA  GCTGCAGCAG  GCAGGAGCTG  CACACACCCA     180
TCCAATTCCA  GCTGCTGATC  TTGATCCTGC  ACCCCGAGCC  GTACACAAGA  GCTAGTCGGT     240
AGAACTTGCA  GGAGCGGAGC  AGAACTAAGT  GCAGAGAACA  GGACATATGG  CTACGCCGGC     300
GGTGA                                                                      305
```

(2) INFORMATION FOR SEQ ID NO:6:

(i) SEQUENCE CHARACTERISTICS:

(A) LENGTH: 3827 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: gst-27 promoter figure 8

(xi) SEQUENCE DESCRIPTION: SEQ ID NO:6:

| | | | | | | |
|---|---|---|---|---|---|---|
| GAATTCCAAA | TATATGATGA | TTGTTGTCCT | AGTGCAGAAG | AACTAAATAT | ACTAGCGAAA | 60 |
| AAAAACCTTC | CTAGTCATGT | AAGTGTATGG | GCATATAGAA | AAATAAACAT | CTCAAGACTC | 120 |
| CAAACTAGTC | ATAGCTTTTA | GTCACAACTT | CAAACACTTC | ATGCCAACAA | GATCATGGAT | 180 |
| TTTTTTTTTT | GCCTAAGACA | AAACTAGAAT | GAGAAAAGAA | CTAACTCATC | ATACATATTA | 240 |
| GTATGGCATC | ACAAAAAAAA | TGACACATAT | ATGATACTAT | ATCACACAGG | CCTTCAGTTT | 300 |
| CTAGAACAAG | TGCAGATCGA | TGTGTGGGTA | TGCATGTCTA | ATATTTACT | AGGTTGGATA | 360 |
| TGCATGGGCG | TTCATTCAGA | ATCAGTTTCA | CACAGTTTAT | CGCACTTCTG | TTTACAAAAC | 420 |
| ATGGATTTCA | TTGCTCTGTA | CTGGCTACAT | GCGTAAGGAT | CAACTTGTCT | AATCTAGGTG | 480 |
| CATCCTCCTT | GTCAAGCAAA | CTTAACAATT | TGATAAAAAA | AAATGCAGCT | TTTATATGTG | 540 |
| AACCCATAAC | TTAATATGGA | CAGGAAACTG | ATGTGCAACA | ACAAAAACTA | AATAGGAAG | 600 |
| GAAACACAAG | TTCCAAATGT | ATAATAATTG | TCACCATAGT | GCAAAGAAC | CAAATATACT | 660 |
| GCAGAGAAAA | CTTCCTAGTC | ATGTAAGTGT | ATGGACATAT | AGAAATAAAA | CATCTCAAGA | 720 |
| CTCCAATAAC | AGGCTCAAGC | TAACTAGTCA | TGGCTTTAAA | CCTTCATGAT | GCAAACTAGT | 780 |
| CACAACTTTA | AACATTTCAT | GCCAACAAGA | TCATGGATGG | TGTTTTTTTT | TCCTAGGGAA | 840 |
| AAGCTAGAAT | GAGAAAAGAC | CTAACTCAGC | ATACATATCA | GGATAGTATC | GTATAGACAC | 900 |
| GTATATGATA | CTATATCACG | CAGCCGTTCA | ATTTCTAGAA | CAAATGCAGA | TTGATCTGTG | 960 |
| AATATGCATG | TCTCATATTT | TACTAGGTTG | GATGGACTGA | ATCCGTGAA | ACAAACAATT | 1020 |
| TATTCAACAA | GTTTCTGCAT | GAATATCATC | TCAAATTCAA | TAATCACTCT | CGTTGATAAA | 1080 |
| AAAATGCAA | CCAACAGTTA | ACCAGAAGTG | AAATAGAAAC | TATTTGAATC | AGATCACTCC | 1140 |
| GTTATTCACA | TCAAAATAAT | TGTTGCTTGA | TCTATAAAAG | CAGTAGGAAC | ATTGTTTACC | 1200 |
| CATCAATTTC | AAGTACACAG | TAACAAGAAC | AGTACAGCTA | GAATTGAGCA | TGTGAGTATT | 1260 |
| GTTGATACCT | CGTTGAGCTC | TCTCTGCCGC | GGCTTTCTGC | TCGGCAGCAA | GAGCCAGCTC | 1320 |
| AGGATCCACC | CCGAAAGCTT | GGGCGTAGGT | GTTGTCTATC | GGCGAAAACA | CGCGCGGTAC | 1380 |
| GCCAAGAACA | GCGCGGCCAT | CTCCATCCCA | GGCACGGTGC | GCCCGCTTTT | CGCCGTCTC | 1440 |
| GCTGAGTCAC | GGCGGGCGTC | CAGCAGGTAG | TTGAGCGCCT | TCCGCGGCAC | GAATCGCTGC | 1500 |
| GTGCGGCCCG | GATCTGGTCG | AGTTGGTAGT | CAGCGTCGGT | GTCGAATGCC | GGGACGTCGA | 1560 |
| CCAGGAAGAA | GTTGCCGTCG | CTGGGGTGGG | GACGGAAGGC | GTCAGGATTG | TCGCAAGGGC | 1620 |
| AGAGCCCAGC | CTGCGGGCGG | GGCTACCTCG | TCGACGCCTC | GGCACGGCGG | CGGCAAAGCT | 1680 |
| GCTGCGGGAC | GTGCCCGCCT | GGGCCGCCTT | CTCGGTGAAG | TGGTCCTCGA | AGGGACGAG | 1740 |
| CTCGCTGGGG | TCAAACCACC | CCATAGCTCG | AGTCACCGAA | GAAGGCGACG | AGGACGAGCC | 1800 |
| CGTCGCGGTG | GCCGCGGTGT | ACCTCCTCGT | CGTCGGTGAG | GCTGACGCTG | TAGATATGGC | 1860 |
| CAGGCCACCA | CGGATGGGAC | TTCACCTTGG | CCCAGACCAT | GTCGCCGAAC | CGGGGCCGC | 1920 |
| CGTTCGCCCA | TGCGATGCCG | CGTCCGGCAG | CAGGAACCAT | GGCGCCTCCA | GCGGCGGGT | 1980 |
| CGGACATCCT | GTGGAGGGGA | ACCGAAAACC | TAGATTTGGA | TGCAGGTTCG | ATTGGTCTGG | 2040 |

-continued

| | | | | | |
|---|---|---|---|---|---|
| GCTTGGGTTT | GGGTTCCGGA | GGAGGGTGGC | CTGGGATCGG | TGGAAGGAGG | GACATTGTTG | 2100 |
| GTAATTTTTA | TTATTTTATA | ATATGGAGAA | ATTCGAGAGA | CTGAACGATG | GTGATGTTTA | 2160 |
| TTTGAGGACT | ATGTAGTATA | AAGTGTAAAA | TAGTATTTTA | TCAAGTTTAT | ATTCACGTTT | 2220 |
| TTGCTGAAGA | TAGTATAATA | GTGGAGTTGT | TTTTGGCGGC | TACATAATCT | TAGGCTATCT | 2280 |
| TCTCGGTCGC | TCTCATATCA | TATCTACTAT | CACATTCTCT | ATTTTAAATT | TCACTTTGTG | 2340 |
| TAATCTACAC | TATAAAATAG | TGTTTTACAC | GGTATGTTGT | ACACAGCCTT | ATCGTGGCGC | 2400 |
| GACGGAGTTG | GATAGAGATG | GTGAACAGCT | GGATAGATAT | GATTATAGG | CGATTGGGTA | 2460 |
| GATGTGATTT | GATAGGTGGT | TATGTAGGAG | CGATTAGTG | AGACATTGTA | AATAATTAGG | 2520 |
| TTGATGTGAT | CCGAGGATGG | CTAGGTAGAT | ATGATTTTAA | TGGATGGTTT | GGTGGACTAA | 2580 |
| GTTATGTGGA | CATTATAATA | TGTTTTAAAT | TTCTAAGAAA | TTGTTTGTGT | TAAATTGTAT | 2640 |
| CCCACATAGA | TTATTTAGCC | ATCTCAAAGA | GAGGTTTGGG | TTGTTTACAC | AAATAAAATA | 2700 |
| TTCGTTTGCT | TCTACAATTT | ATATGTTTTT | TATTTACATG | AAAACTATAT | TTTTTATTCA | 2760 |
| TCTACTCACC | CAGCACAGAA | ATTCTGGTTG | AGTAGATGAA | AAAAAACTAC | AACAAACTCT | 2820 |
| TCCTGAAAGT | GTCGGTGTGA | AGCCGAGAAA | TCCTTTTCAT | TTCGGTGACG | GAGCCCCTTG | 2880 |
| CTGGCTGCTG | CTCAGTGCAC | TCCGTTCGCC | TGCCTGCCAC | TACAAGCGAC | GGCCGACGAC | 2940 |
| TCGCAAGTAT | CGGTAGGCAT | TTTAAAACTG | AAAACCAAAT | CTAAACCCGA | ATAGACCAAA | 3000 |
| TTGTTGGTTT | ATTCGGGTTT | TTGGGTTCGG | ATTCGGTTTC | TAAATATGCT | ATATTTTAGG | 3060 |
| GTATAGGTTC | GGGTTCAGTT | TCTAACCTTT | AAAACCTGAA | TAGACGAATA | ACCCGAAATA | 3120 |
| TAAAAAATCT | CTTAATATGT | GATGATATTA | TTATATGATT | TATGAACTTA | TTAACCGAAA | 3180 |
| ATAATGATAC | CATCCTAACG | ATAGTATATA | TATCTATGTA | TGCTATTTTT | ATAGTCACTT | 3240 |
| GTTGTAATAA | TAGTACTTCC | AATTAATTAA | TCAGTGTATA | TATTTAACA | AAAGATACTA | 3300 |
| GCCTCTCTAC | TATTTGAGTA | TATTCGGTGC | ACCGAATAGA | CCGAACCGAA | ATTGTAAGTC | 3360 |
| TATTCAGGTT | CGGTTCCTAA | AATTATTTTA | AAAATTTTGG | TTCTCATATT | TCAGAATCCG | 3420 |
| AAATTTCATA | AATCCAAATA | GACCGAACCA | AATTACGCTA | ATAGACCGAA | TAACTAGCGT | 3480 |
| ACTCGCAAGT | CGCACCCCAC | TAGCCTGCTG | CGTGCGTAAG | CGAGGACGTC | ACGCGTTCTC | 3540 |
| CCTCCCGTCG | ACCAAATACA | CTTGGTCTTC | TAGCACCTTC | TTCCTCTCCA | AGACTCCAAT | 3600 |
| CCCCCAACCA | CCAGAACCAG | CGCCAGCTCT | AACGTCACCT | CTGATTTCTC | TCTCCTCTCT | 3660 |
| ATTGCTAGCT | GCTTTATTAT | AAGTAGCAGC | TGCAGCAGGC | AGGAGCTGCA | CACACCCATC | 3720 |
| CAATTCCAGC | TGCTGATCTT | GATCCTGCAC | CCCGAGCCGT | ACACAAGAGC | TAGTCGGTAG | 3780 |
| AACTTGCAGG | AGCGGAGCAG | AACTAAGTGC | AGAGAACAGG | ACATATG | | 3827 |

( 2 ) INFORMATION FOR SEQ ID NO:7:

( i ) SEQUENCE CHARACTERISTICS:
      ( A ) LENGTH: 119 base pairs
      ( B ) TYPE: nucleic acid
      ( C ) STRANDEDNESS: both
      ( D ) TOPOLOGY: linear ( i i ) MOLECULE TYPE: cDNA ( x i ) SEQUENCE DESCRIPTION: SEQ ID NO:7:

| | | | | | |
|---|---|---|---|---|---|
| CCAGCTGCTG | ATCTTGATCC | TGCACCCCGA | GCTGTACACA | AGAAGCTAGT | CGGTAGAACT | 60 |
| TGCAGGAGCG | GAGCAGAACT | AAGTGCAGAG | AACAGGACAT | ATGGCTACGC | CGGCGGTGA | 119 |

PLANT-DERIVED ENZYME AND DNA SEQUENCES AND USES THEREOF

This is a division of application Ser. No. 08/170,294, filed as PCT/GB92/01187, Jul. 1, 1992, now issued as U.S. Pat. No. 5,589,614.

This invention relates to a glutathione-S-transferase enzyme and DNA sequences coding for it.

BACKGROUND OF THE INVENTION

Glutathione-S-transferases (GST) are a family of enzymes which catalyse the conjugation of glutathione, via a sulphydryl group, to a large range of hydrophobic, electrophilic compounds. The conjugation can result in detoxification of these compounds and may result in their removal from tissue.

GST enzymes have been identified in a range of crop plants including maize, wheat, sorghum and peas. GST's comprise from 1 to 2% of the total soluble protein in etiolated maize seedlings.

Three isoforms of GST have been identified: GST-I, GST-II and GST-III. The major isoform in maize tissue, GST-I, is constitutively expressed and is capable of conjugating glutathione with pre-emergent herbicides such as alachlor. Treatment of maize tissues with chemical safeners (for example, N,N-diallyl-2,2-dichloroacetamide) raises the activity of GST-I which participates in the detoxification of the pre-emergent herbicides.

International Patent Application WO 90/08826 describes GST-II (isoform II).

Both GST-I and GST-II proteins have a native molecular weight of approximately 50 kD. As in mammals, maize GST's are dimeric; GST-I has apparently identical polypeptide subunits of 29 kD (GST-I-29), whereas GST-II is a heterodimer of a 29 kD subunit identical to that found in GST-I (GST-I-29) and a novel 27 kD subunit (GST-II-27). GST-II is detected at a very low basal level in the absence of safener, but its expression is enhanced dramatically by safener treatment. Like GST-I, GST-II confers resistance to certain herbicides. GST-II is known to detoxify chloroacetanilide and thiocarbamate herbicides such as alachlor (Mozer et al, 1983, Biochemistry, 22:1068–1072).

A cDNA and a gene corresponding to the 29 kD subunit of GST-I have been cloned previously and sequenced (Wiegand et al, 1986, Plant Mol Biol, 7:235–243). In addition, a cDNA corresponding to a 26 kD subunit of a third, minor component of GST activity in maize seedlings (GST-III-26) has been previously cloned and sequenced (Moore et al, 1986, Nucleic Acid Research, 18:7227–7235). GST-III is a homodimer of these 26 kD subunits. Like GST-I and unlike GST-II, GST-III is constitutively expressed. It is known to detoxify herbicides such as atrazine.

SUMMARY OF THE INVENTION

According to the present invention, we provide a genomic DNA sequence encoding the gene promoter for the 27 kD subunit of the glutathione-S-transferase, isoform II, enzyme (GST-II-27), containing the nucleotide sequence shown in FIG. 8 herewith and variants of the said sequence as permitted by the degeneracy of the genetic code.

The genomic DNA was deposited on Jun. 14, 1991 in the National Collections of Industrial and Marine Bacteria (NCIMB), 23 St Machar Drive, Aberdeen, AB2 1RY, Scotland, UK, as plasmid pGIE7 contained within *Escherichia coli*, strain XLI-Blue with the accession number NCIMB 40426.

The invention also provides a GST-II-27 enzyme subunit having the amino acid sequence shown in FIG. 3 herewith.

The invention further provides a cDNA sequence encoding this GST-II-27 subunit, having the nucleotide sequence shown in FIGS. 2A–2C herewith and variants of the said sequence as permitted by the degeneracy of the genetic code.

The cDNA was deposited on Apr. 19, 1991 in the National Collections of Industrial and Marine Bacteria (NCIMB), 23 St Machar Drive, Aberdeen, AB2 1RY, Scotland, UK, as plasmid pIJ21 contained within *Escherichia coli*, strain XLI-Blue with the accession number NCIMB 40413.

International Patent Application WO 90/08826 describes a chemically inducible gene promoter sequence isolated from a 27 kD subunit of the maize GST-II gene (GST-II-27). The said International application is incorporated herein by reference.

In the present application we describe the cloning and sequencing of a complete cDNA corresponding to the 27 kD subunit. This sequence is inducible and specifically recognised by a GST-II-27 specific antiserum. It is partially homologous with other maize GSTs.

By virtue of the present invention, the cDNA for GST-II-27 has been utilised as a gene probe for the isolation of a corresponding genomic sequence which includes the promoter region.

The invention further provides a chemically switchable gene construct which includes the GST-II-27 gene promoter operatively linked to a foreign gene or a series of foreign genes whereby expression of said foreign gene or said series of genes may be controlled by application of an effective exogenous inducer. The invention also provides plants transformed with said gene construct.

The GST-II-27 gene has been shown previously (International Application Number WO 90/08826) to be induced by certain chemical compounds, known as "herbicide safeners", which can be applied, as a spray, for example, to growing plants. Induction may be achieved by application of any suitable chemical including known safeners and other agrochemicals, chemical analogues and other potential inducers. Such chemicals may include N,N-diallyl-2,2-dichloroacetamide (common name: dichloramid); 2,2.5-trimethyl-3-(dichloroacetyl)-1,3-oxazolidine; benzyl-2-chloro-4-(trifluoromethyl)-5-thiazole-carboxylate (common name: flurazole); naphthalene-1,8-dicarboxylic anhydride; 2-dichloromethyl-2-methyl-1,3-dioxolane; 1-(dichloroacetyl)-hexahydro-3,3,8a-trimethyl-pyrrole (1,2-a)-pyrimidin-6(2H)-one; 1,3-dioxolan-2-ylmethoxyimono (phenyl)benzene acetonitrile; 4,6-dichloro-2-phenyl-pyrimidine; 2,2-dichloro-[N-allyl-N(1,3-dioxalano-2-methy)]acetamide; 1-(cyanomethoxyimino) benzacetonitrile; 4'-chloro-2,2,2-trifluoroacetophenone-O-1,3-dioxolan-2-yl methyloxime; 2,2-dichloro-1-(3,4-dihydro-3-methyl-2H-1,4-benzoxazin-4-yl) ethanone; 3-dichloroacetyl-2,2-dimethyloxazolidine; 4-methoxy-3,3-dimethylbenzophenone;1-cyclohexyl-4,4-dimethyl-2-(1H-1,2,4-triazol-1-yl) pent-1-en-3-ol;2,2-dichloro-N-(3-methyl-4-thiazolin-2-ylidene) acetamide; O,O-diethyl-O-phenyl phosphorothioate; 2,2-spirocyclohexyl-N-dichloroacetyl oxazolidine; N-benzyl-N-ethyl-dichloroacetamide; 3-chloroacetyl-4,4-cyclohexane-spiro-2,2-dimethyl-1,3-oxazolidine; spirooxazolidine acetamide; oxabetrinil; cyometrinil; fenclorim; methoxyphenone.

The GST-II-27 promoter, then, when linked to an exogenous or foreign gene and introduced into a plant by transformation, provides a means for the external regulation of expression of that foreign gene. The foreign gene may be any gene other than the wild type GST-II-27 gene. The said International Patent Application WO 90/08826 provides details of the manner of use of such an externally regulatable promoter and International Patent Application Number WO 90/08830 describes in detail the use of such promoter as a component of a gene cascade leading to regulation of male sterility in plants and the uses of such plants in the production of hybrid crops. It is shown here that the inducible GST-II-27 promoter is functional in both monocotyledons and dicotyledons. It can therefore be used to control gene expression in a variety of genetically modified plants, including field crops such as canola, sunflower, tobacco, sugarbeet, cotton; cereals such as wheat, barley, rice, maize, sorghum; fruit such as tomatoes, mangoes, peaches, apples, pears, strawberries, bananas and melons; and vegetables such as carrot, lettuce, cabbage and onion. The GST-II-27 promoter is also suitable for use in a variety of tissues, including roots, leaves, stems and reproductive tissues.

In general outline, the procedures which were used in isolating the enzyme, the cDNA and the genomic DNA of this invention were as follows:

Total RNA was extracted from safener-induced maize tissue at the peak of GST activity, and used to construct a cDNA library which contained GST transcripts.

The GST-II-27 protein was extracted from the same type of tissue, purified and used to raise a sheep antiserum (characterised by western and dot blot analysis).

By immuno-screening the cDNA library with this antiserum (using an isotopic detection system), the new GST sequence was isolated. Plaque purification allowed in vivo excision and sequencing of the plasmid DNA containing this GST. Northern analysis showed that it was a safener-inducible clone.

GST-II-27 genomic clones were isolated by screening a maize genomic library with a carefully designed probe prepared from the above cDNA. By mapping these clones, a fragment containing the promoter region was isolated and sequenced.

The promoter sequence was used to construct plant gene expression cassettes. These cassettes were introduced into both monocotyledons and dicotyledons and shown to control gene expression in an inducible manner.

The invention further provides a method to produce a herbicide resistant transgenic plant which comprises the incorporation of DNA encoding GST polypeptides into the plant such that a glutathione-S-transferase enzyme is expressed. The invention also provides herbicide resistant plants produced by said method, and their progeny.

The purpose in providing crop plants which resist the action of a herbicide is to facilitate the control of weeds growing between the plants by the overall application of an effective concentration of a herbicide which would destroy the crop plant in its normal, that is herbicide sensitive, state. Such resistant plants are also useful for use in a locus of any short term carry-over of herbicide from a previous application. In this context, a resistant plant is defined as one which displays enhanced tolerance to a herbicide when compared to a standard plant. Resistance may vary from a slight increase in tolerance to the effects of the herbicide to total resistance where the plant is unaffected by the presence of herbicide.

Herbicidal tolerant plants containing a glutathione-S-transferase gene have been described in Australian patent Application 73146/87 (Ciba Geigy) published on Nov. 26, 1987 (related to U.S. Pat. No. 5,073,677 published on Dec. 17, 1991). The patent application describes the use of mammalian GST sequences, specifically a rat sequence. The genetic sequence coding for a rat GST is disclosed and used to construct plant transformation vectors for tobacco; some transformants showed atrazine resistance. The patent application does not describe GST sequences derived from plants; in particular, it does not disclose the GST-II-27 sequence.

DNA encoding GST polypeptide subunits may be incorporated into a plant transformation vector under the control of a suitable promoter (constitutive or inducible). A plant expressing GST-I 29 kD polypeptide subunits will show GST-I enzyme activity. A plant co-expressing GST-I 29 kD subunits and GST-II 27 kD subunits will show GST-II enzyme activity, and some GST-I activity. A plant expressing GST-III 26 kD subunits will show GST-III enzyme activity. A plant co-expressing GST-I 29 kD and GST-III 26 kD subunits will show GST-I and GST-III activity. A plant co-expressing GST-I 29 kD, GST-II 27 kD and GST-II 26 kD polypeptide will show GST-I, GST-II and GST-III activity. All such plants will be capable of conjugating glutathione with certain pre-emergent herbicides: they will thus be resistant to these herbicides. GST activity is known to be effective against a range of chemical herbicides, including the chloroacetanilides and the thiocarbamates, and may be active against other compounds which show herbicidal properties. The actual spectrum of herbicide resistance displayed by the transgenic plant will depend on which GST isoform is active (GST-I, GST-II or GST-III) or on the relative activity of the various GST isoforms present in the plant. For example, GST-II is active against alachlor and acetochlor; GST-III is active against atrazine. Thus the method of producing herbicide resistant transgenic plants may be used not only to confer resistance on previously susceptible plants or to increase existing resistance, but also to broaden the range of herbicides to which the plant is resistant. So the ability to introduce multiple resistances by expressing the various GST isoforms within the transgenic plants is advantageous for agricultural purposes. Specific resistance to a particular herbicide may be achieved by incorporation of the specific GST isoform (or combination of isoforms) which is most effective against this herbicide. In particular, the presence of GST-II activity in the plant may provide resistance to certain herbicides which cannot be detoxified by the GST-I or GST-III enzymes. Thus the ability to produce plants in which herbicide resistance is conferred by GST-II activity (via transformation with the GST-II-27 sequence) will be advantageous.

Plants may be transformed with constructs containing sequences which encode GST subunits according to a variety of known methods (Agrobacterium Ti plasmids, electroporation, microinjection, microprojectile gun, etc). The transformed cells may then in suitable cases be regenerated into whole plants in which the new nuclear material is stably incorporated into the genome. Both transformed monocot and dicot plants may be obtained in this way, although the latter are usually more easy to regenerate. Examples of genetically modified plants which may be produced include field crops such as canola, sunflower, tobacco, sugarbeet, cotton and cereals such as wheat, barley, rice, sorghum and also maize.

Some plant species do not naturally contain GST enzymes which can detoxify herbicides. Incorporating DNA encoding GST polypeptides into such species will thus confer new or additional resistance to certain herbicides. Although GSTs are naturally expressed in other species, notably maize, production of transgenic plants containing enhanced levels of GSTs may increase the crop's level of herbicide resistance. In addition, all the GST isoforms are not normally present in all maize lines. Production of transgenic maize containing one or more additional GST isoforms will confer resistance to a wider range of herbicides. A further advantage comes from placing the GST-II-27 sequence under control of a constitutive promoter, as this will mean that the GST-II enzyme is constitutively expressed within the transgenic maize plant. This avoids the need to apply a chemical safener to the maize seed or plant. Normally, GST-II enzyme activity is inducible. It is current practice to apply a safener (such as dichloramid) as a seed coating to induce GST-II enzyme activity in the emerging plant, thus conferring herbicide resistance.

Amino acid sequencing has shown that the 29 kD subunit of GST-I is identical to the 29 kD subunit of GST-II. Thus a combination of the GST-I-29 subunit and the GST-II-27 subunit will give an active GST-II enzyme. Co-expression of the cDNA encoding GST-I-29 (isolated by Wiegand et al, 1986, Plant Mol Biol, 7:235–243) and the cDNA encoding GST-II-27 (as shown in FIGS. 2A–2C) within a transgenic plant will give a plant with GST-II activity.

DNA encoding the GST-I 29 kD subunit or the GST-II 27 kD subunit may be incorporated into a vector under the control of a suitable promoter such as the 35S CaMV promoter. Plants may be transformed with vectors containing either the GST-I-29 or the GST-II-27 expression cassette. Transformants expressing the respective GST-II subunits (29 kD or 27 kD) may be crossed to produce progeny expressing both GST-I-29 and GST-II-27, resulting in a herbicide resistant phenotype. In a modification of this method, each plant may be co-transformed with vectors containing the GST-I-29 expression cassette and with vectors containing the GST-II-27 expression cassette. Alternatively, DNA encoding the GST-I 29 kD subunit and the GST-II 27 kD subunit may be included in a single plant transformation vector under the control of a single promoter. Transformants expressing both GST-II subunits (29 kD and 27 kD) will show a herbicide resistant phenotype; transformants expressing only one of the respective GST-II subunits (29 kD or 27 kD) may be crossed to produce progeny expressing both subunits.

The above methods can be adapted to produce herbicide resistant plants expressing the GST-I enzyme (transformation with DNA encoding GST-I-29), the GST-II enzyme (transformation with DNA encoding GST-III-26, as isolated by Moore et al, 1986, Nucleic Acid Research, 18:7227–7235), or some selection of GST-I/GST-II/GST-III activity.

Preferably, DNA encoding the GST subunits is introduced into the plant under control of a constitutive promoter (such as the 35S CaMV promoter). This avoids any need for external induction of GST expression: the plant is permanently herbicide resistant. DNA encoding the GST subunits may also be included in a plant transformation vector under the control of an inducible promoter, to give inducible herbicide resistance in the transgenic plants. Such a promoter includes the chemically-inducible GST-II-27 promoter as shown in FIGS. 7A–7C. Resistance may be switched on by application of a suitable inducer (such as a chemical safener). In certain circumstances, the ability to express or to increase herbicide resistance only when required may be advantageous. For example, during rotation of crops, individuals of the first crop species may grow the following year in the field to be cultivated with a second crop species. A herbicide may be used to destroy these un-induced and still susceptible "volunteer" plants. Induction of GST expression only when herbicide resistance is required (that is, just before application of a herbicide) may also be metabolically more efficient in some circumstances as the plant is producing GST polypeptides only when required.

The invention will now be described by way of illustration in the following description, which gives details of the isolation, expression studies and sequencing of GST-II-27, the construction of inducible expression cassettes and demonstration of their functioning in transgenic plants, plus the production of herbicide resistant plants.

BRIEF DESCRIPTION OF THE DRAWINGS

FIGS. 2A–2C show the nucleotide sequence of cDNA encoding GST-II-27 (SEQ ID NO:1).

FIG. 3 shows the amino acid sequence of GST-II-27 compared to the amino acid sequences of GST-I-29 and GST-III-26 (SEQ ID NO:2 through SEQ ID NO:4).

FIG. 4 shows primer extension mapping of the genomic clones (SEQ ID NO:5 and SEQ ID NO:7).

FIGS. 7A–7C show the nucleotide sequence of the GST-II-27 promoter (SEQ ID NO:6).

DETAILED DESCRIPTION OF THE INVENTION

Safener Treatment of Corn Tissue

For treatment of young maize seedlings, seeds were germinated on moist filter paper. After germination and growth (up to one week) the safener N,N-diallyl-2,2- dichloroacetamide (hereinafter referred to as R-25788) was added to the water in the filter paper and the seedlings grown for a further time period before harvesting of tissue.

Enzyme Assay

Enzyme activity was measured spectrophotometrically at 340 nm using 1-chloro-2,4-dinitrobenzene (CDNB) as a substrate. The reaction buffer contained 0.1M EDTA, 0.001M CDNB and 0.0025M glutathione.

Preparation of Extracts & Enzyme Purification

Tissue was homogenised in 0.05M Tris.HCl, pH 7.8; 0.001M EDTA; 0.001M DTT; and 7.5% polyvinylpyrrolidone in a pestle and mortar, at 4° C., and centrifuged at 30,000 g to obtain a crude extract.

Separation of the GST isoforms from the crude extract was achieved as follows: the crude extract was applied to a DEAE Sepharose column and washed with 0.01M Tris.HCl, pH 7.8; 0.001M EDTA; and 0.001M DTT. The bound GST was eluted with 0.3M potassium chloride. Fractions containing GST activity were combined and desalted using PD10 gel filtration columns. Separation of the GST I and GST II isoforms was achieved by FPLC on a mono-Q column and a zero to 0.4M potassium chloride concentration gradient.

Pure samples of GST I and GST II were obtained by applying desalted fractions of GST I and GST II from the FPLC to a glutathione-S-sepharose affinity column equilibrated with 0.05M phosphate buffer at pH 7.3. After washing with buffer, bound GST was eluted with 0.005M glutathione.

SDS-PAGE (17.5%, 30:0.174 acrylamide:bisacrylamide) of GST I or GST II was achieved by concentrating pure GST samples using Amicon Centricon 10 Microconcentrations (Trade Mark), denaturing samples in mercaptoethanol containing Laemmli buffer, and staining the gels with Coomassie Blue.

Inductible Expression of GST

Figure 1:
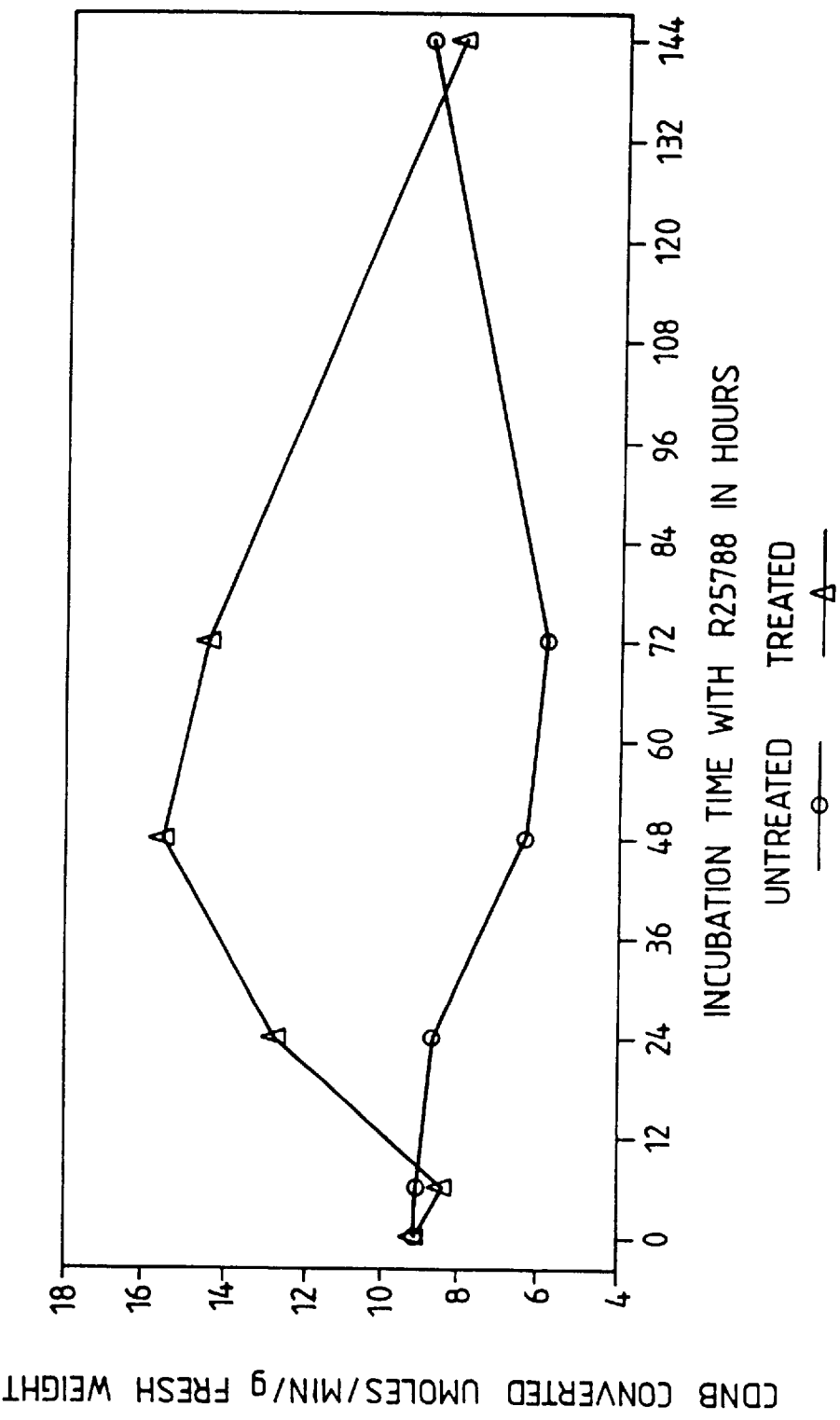
FIG. 1 is a time course graph showing GST activity in induced and uninduced maize root tissue.

A time course experiment was carried out to examine the expression of GST's after safener treatment. A 30 ppm solution of R-25788 was applied to three-day old seedling roots and tissue harvested after various time intervals following safener treatment. Samples were tested for GST activity using the enzyme assay described above. The results of this experiment are presented graphically in FIG. 1. This shows there was an approximate 2.5 fold increase in total GST activity after 48 hours incubation.

Construction of cDNA Libraries

The time course experiments revealed a peak of GST expression at 48 hours after treatment with safener. Therefore, two cDNA libraries were constructed from total RNA extracted from root tissue at 24 and 48 hours after safener treatment.

To ensure that the induction procedure had been successful, a one gram sample of 24 hour induced tissue was taken and assayed for GST II. This experiment revealed that the tissue used to construct the cDNA library had indeed been successfully induced as GST II accounted for about 25% of the total GST activity.

Double-stranded cDNA was prepared from oligo dT-cellulose-purified RNA by a method employing RNase and *E coli* DNA polymerase I in the synthesis of the second strand, without prior purification of single-stranded cDNA (Gubler and Hoffman, 1983). Lambda ZAP II was chosen as the cloning vector.

Generation of Antibodies to the GST-II-27 Enzyme

Sufficient protein to enable the immunisation of sheep was obtained by pooling the enzyme subunit isolated as described above from a number of separate experiments. The 27 kD GST II polypeptide was subsequently purified to apparent homogeneity by electroelution from polyacrylamide gel slices. Antisera were prepared against the 27 kD polypeptide. The immunisation of sheep was carried out essentially according to Stewart and Rowe (1975, J Immunological Methods, 8:37–45).

Western blotting experiments showed that a specific recognition of the GST-II 27 kD subunit was obtained using an antiserum. Furthermore, no cross-reactivity with the GST-II 29 kD subunit was obtained. The affinity and specificity of the primary antiserum was tested by immuno dot blotting and western blotting, showing no cross reactivity with other polypeptides in crude extracts.

A variety of control experiments were carried out to optimise the primary and secondary antibody concentrations, to test various enzyme substrates, and to validate fusion protein induction conditions. Conditions which maximised the signal to background noise ratio were identified, and allowed detection of 1 ng GST-II 27 kD subunit.

Immuno-screening of the cDNA Libraries

In order to identify a cDNA clone encoding maize GST-II-27, bacteriophage from the cDNA library were screened.

Immuno-screening using a $^{125}$I protein G detection system allowed detection of 0.1 ng of denatured GST-II-27.

$1 \times 10^6$ recombinants from the safener induced seedling library were screened at high plating densities ($3 \times 10^4$ per plate). 30 positive plaques were detected, picked and rescreened using overnight incubation with IPTG soaked filters. Six strongly positive candidates remained after 3 rounds of plaque purification.

Further Plaque Purification

A fourth round of plaque purification was carried out using immuno-screening and DNA hybridisation (with the cDNA probe isolated by PCR from the third screen). Six clones came through plaque purification with both detection methods. Furthermore, the DNA probe cross-hybridised at equal intensities with all 6 positive clones, indicating they probably represented the same sequence.

Isolation of Plasmid DNA

The in vivo excision protocol (Stratagene) was carried out to liberate Bluescript phagemids. Plasmid DNA prepared from four different lysates was designated pIJ13, pIJ15, pIJ17 and pIJ21 respectively.

Plasmid pIJ21 was deposited in the National Collections of Industrial and Marine Bacteria (NCIMB), Aberdeen, with the accession number NCIMB 30 40413.

Characterisation of Library Positive Clones

When digested with EcoRI all clones liberated a single insert of between 900–950 base pairs, which is the predicted insert size to encode a 27 kD protein. When the gel was blotted and hybridised with pIJ17 all inserts hybridised with equal intensities.

The 950 base pair insert from one of the clones was hybridised to a Southern blot of GST-I-29 and GST-III-26 PCR products. The experiments showed no hybridisation to GST-III-26 and a very weak hybridisation to GST-I-29 (1 μg target DNA with overnight exposure). When the Southern was stripped and rehybridised with a GST-I-29 specific probe, only a 15 minute exposure was required.

The 950 base pair insert (the putative GST-II-27 PCR product) and the GST-I-29 specific oligo were also used to probe library filters of $1 \times 10^6$ recombinants. Different hybridisation patterns were obtained for each probe.

These studies indicate the positive clone from the library was not GST-I-29 or GST-III-26, but did share some weak homology with GST-I-29.

Sequence Analysis of cDNA

Between 200–300 bases of the 3' and 5' ends of each clone was sequenced using SK and KS primers. These data showed the four clones (pIJ13, pIJ15, pIJ17 and pIJ21) to be identical, except for the position of the poly A tail. As with GST-I-29 three possible poly A addition sites were identified.

The longest clone pIJ17KS was fully sequenced: the cDNA sequence (954 base pairs) is shown in FIGS. 2A–2C. The sequence of pIJ17KS shows homology in the central region with maize GST-I-29 and GST-III-26, which provided strong evidence that this clone represents a maize GST. However, the region of high homology between GST-I-29 and GST-III-26 at the 5' end is dissimilar to the 5' region of pIJ17KS, showing that the latter codes for a different protein.

Analysis of the coding region of GST-II-27 shows it to be a G-C region and to contain several repeats in the 5' region.

Evidence that pIJ17KS Encodes an Inducible GST

Expression studies carried out by northern analysis strongly suggested that pIJ17KS corresponds to a GST-II-27 sequence. pIJ17KS strongly hybridised to a 0.95 kB transcript in induced RNA (I) isolated from a range of treated tissues including roots (R), tassel (T), silks (S) and leaf (L). With uninduced RNA (U), there was a poor hybridisation signal or in some cases no signal. Control hybridisation with a constitutive probe indicated equal loadings of RNA for the induced and uninduced samples. This indicates that pIJ17KS indeed represents a safener inducible clone. Densitometry analysis shows a 100 fold induction in the 0.95 kB transcript in certain tissues such as leaf after safener treatment.

The presence of a signal in uninduced RNA supports previous western data which detected a low basal expression of GST-II 27 kD subunit in the absence of safener treatment.

Amino Acid Sequence of GST-II-27

Pure samples of GST-II were obtained by Sulphobromophthalein Glutathione-S-Agarose affinity chromatography. To separate the 27 kD and 29 kD subunits, the GST-II was injected onto a C8 Reverse Phase HPLC column (SGE 100 mM×2.1 mM , 300 Å pore). The subunits were eluted with a gradient of acetonitrile in 0.1% Trifluoroacetic Acid. SDS PAGE (17.5% T ,0.6% C) identified the UV absorbing peaks that corresponded to the 27 kD and 29 kD subunits.

The total amino acid composition of each subunit was determined using an Applied Biosystems 420AH Derivatizer Automated Amino Acid Analyser. This showed that there was close agreement between the measured composition and that predicted from the nucleic acid sequence for both the 29 kD and 27 kD subunits.

N-terminal sequence analysis was performed on each subunit by Edman Degradation using an Applied Biosystems 477 Pulsed Liquid Phase Automated Amino acid Sequence Analyser. This showed that the N-terminal sequence of the 29 kD subunit is identical to the 29 kD subunit of GST-I. The N-terminus of the GST-II 27 kD subunit was blocked to Edman Degradation.

Reverse phase HPLC separated GST-II-27 was freeze dried in a Univap freeze concentrator. Each subunit was reduced using 6M Guanidine-HCL and 45 mM Dithiothreitol at 50° C. for 15 minutes and then alkylated with 8 mM Iodoacetamide at 20° C. for 15 minutes. The protein was diluted to produce a 2M Guanidine-HCL solution and Endoproteinase Lysine C added (1:20 protease:GST). Protease digestion was performed overnight at 37° C. (Stone et al; Chap. 2 in "A Practical Guide to Protein and Peptide Purification for Microsequencing" ed. Matsudaira, Academic Press). The digest was injected onto a C8 Reverse Phase HPLC column (SGE 2.1*100 mM ) and a gradient of acetonitrile in 0.1% Trifluoroacetic acid used to elute the peptide fragments . Amino Acid sequence analysis of one fragment gave sequence corresponding to amino acids 208–222 of GST-II-27 as predicted from the nucleic acid sequence. This sequence has no homology with the published sequence for GST-I-29 or GST-III-26.

Further amino acid sequence was obtained by digesting the reduced and alkylated GST-II-27 with trypsin for 2.5 hours at 20°0C. The peptides were separated by Reverse Phase HPLC ( using a Vydac C8 4.6*150 mM, 300 Å pore column) and a gradient of acetonitrile. Three peptides were sequenced and these sequences corresponded to amino acids 8–19, 20–38 and 52–71 of GST-II-27 as predicted from the nucleic acid sequence. This shows that the isolated cDNA clone corresponds to the GST-II-27 subunit.

FIG. 3 compares the amino acid sequences of GST-II-27, GST-I-29 and GST-III-26. An asterisk (*) indicates a position in the alignment is perfectly conserved; a dot (.) indicates a position is well conserved; a tick (✓) indicates a position which is conserved with rat GSTs. GST-II-27 shows homology to the two known isoforms, GST-I-29 and GST-III-26. GST-II-27 is 57% identical with GST-I-29 and 41% with GST-III-26. Furthermore, several residues are conserved with rat GSTs.

Genomic Clone Isolation

The cDNA for GST-II-27 was utilised to design a gene probe for the isolation of a corresponding genomic sequence which included the promoter region.

The GST-II-27 cDNA sequence was examined to identify a specific region which does not occur in other maize GSTs or other plant/animal/viral/vector sequences, and hence would be suitable as a specific gene probe. A 208 bp sequence was isolated by PCR from the 3' end of plasmid pIJ21 and purified by acrylamide gel electrophoresis. This PCR probe was random prime labelled and used to screen 5×10⁶ recombinants from a maize genomic library (partial MboI digested DNA with an average insert size of 15 kB).

The positive clones were plaque-purified with the 3' PCR probe and a 5' oligo (130 bp from the 5' end of the cDNA). These genomic clones were then mapped to identify fragments running from the 5' end of the cDNA into the promoter region. An EcoRI fragment containing around 4 kB of promoter region was isolated. This fragment was subcloned into a pBS vector, designated plasmid pGIE7, which was deposited in the National Collections of Industrial and Marine Bacteria (NCIMB), Aberdeen, with the accession number NCIMB 40426.

Primer extension analysis (as described by Ausubel et al, 1987, Current Protocols in Molecular Biology) was used to map the transcription start point (TSP) to 16 bp from the end of the cDNA as shown in FIG. 4. Sequence analysis of the promoter subclone pGIE7 revealed putative TATA and CAAT boxes −29 bp and −110 bp from the predicted TSP respectfully. The TSP site, TATA box and intron/exon boundary regions fit the plant consensus sequences, confirming that the isolated sequence is indeed the promoter sequence.

Sequencing of the GST-II-27 Promoter Fragment

Figure 5:
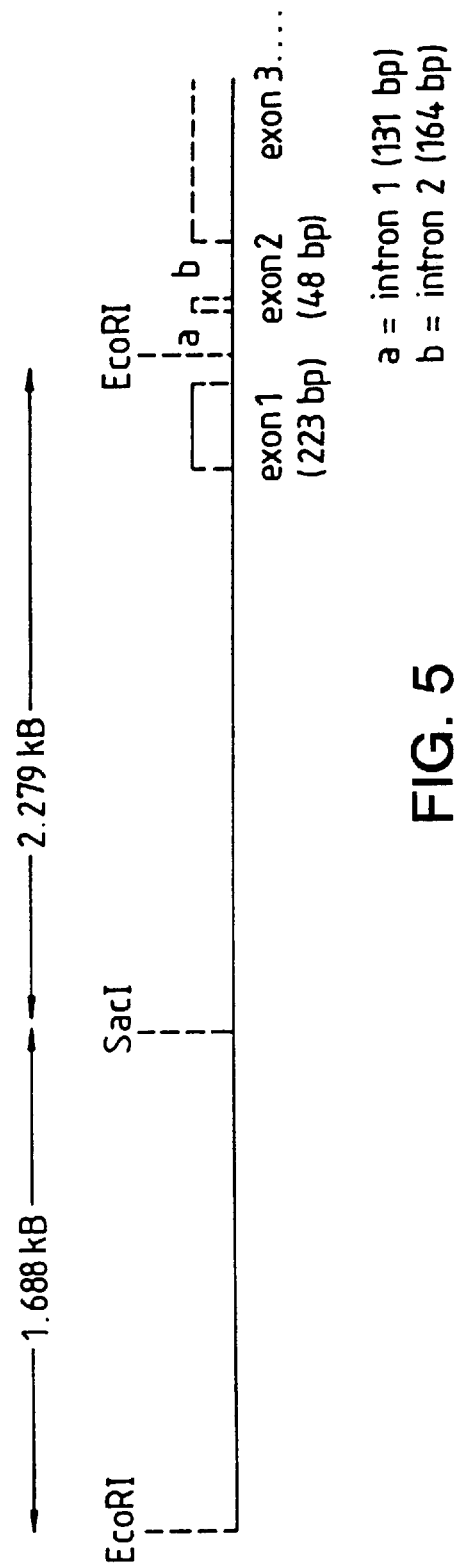
FIG. 5 represents the 5' end of the GST-II-27 gene.

FIG. 5 represents the 5' end of the GST-II-27 gene, showing the relative position of restriction sites and the EcoRI fragment isolated above. PCR and restriction analysis of the genomic clones had indicated that two introns covering 300 bp are present in the region corresponding to the 5' end of the cDNA, and that one of the introns contains an EcoRI cleavage site. Plasmid pGIE7 is contains the EcoRI-EcoRI fragment which covers the GST-II-27 promoter region plus some coding sequence. The sequence of exon 1 (underlined) matches that of the 5' end of the cDNA.

Figure 6:
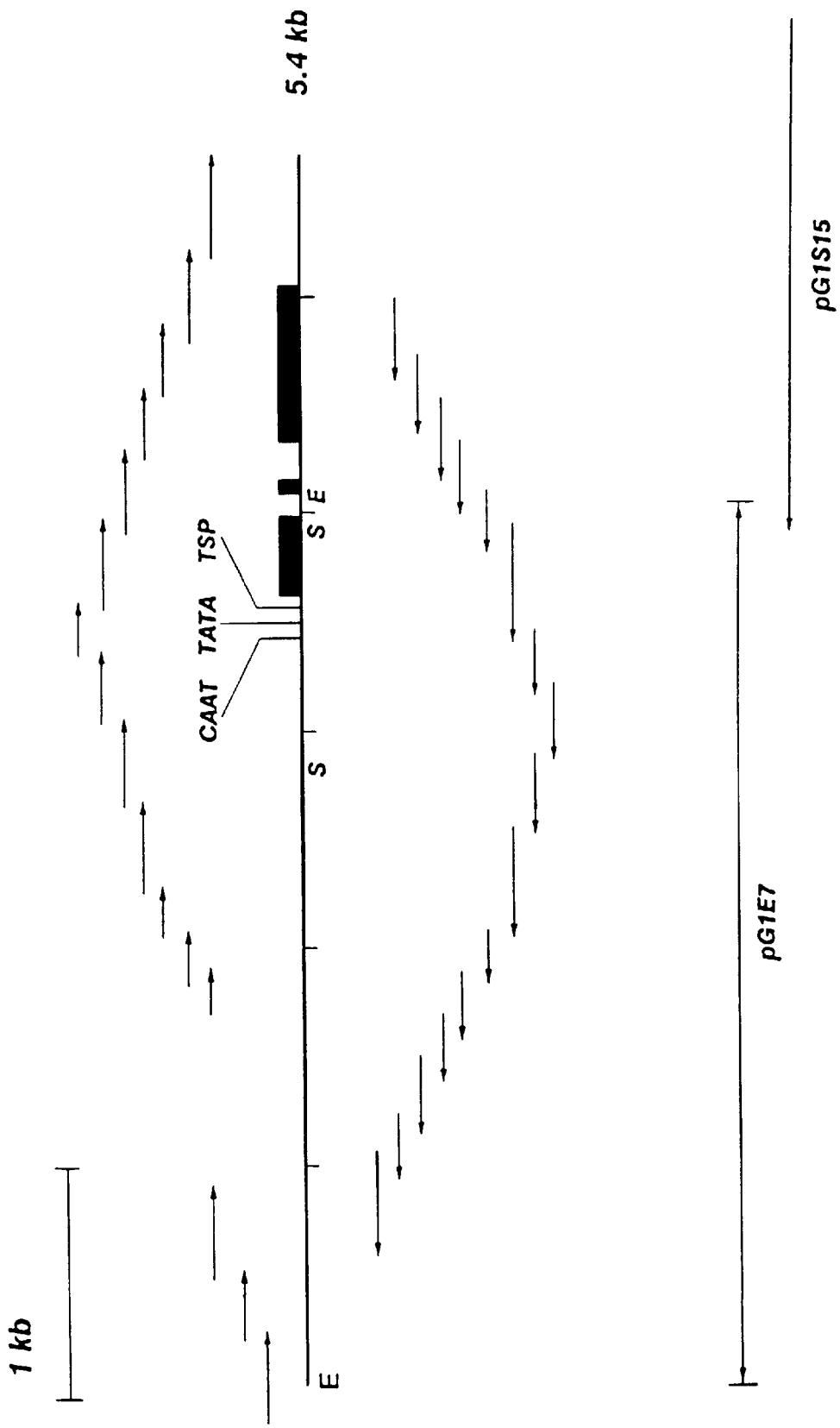
FIG. 6 shows the strategy used to sequence 5.4 Kb of the GST-II-27 gene and promoter.

Genomic subclones pGIE7 and pGIS15 were used to sequence 5.4 Kb of the GST-II-27 gene and promoter. The majority was sequenced on both strands according to the strategy illustrated in FIG. 6. FIGS. 7A–7C show the nucleotide sequence of 3.8 kB of the promoter sequence from the 5' EcoRI site to the predicted translation start point.

GST-II-27 Promoter Constructs

Using a combination of fine mapping of promoter subclones and sequence data, appropriate restriction sites were chosen for promoter constructs. A variety of transient assay vectors for protoplast systems (pPUG) and stable transformation vectors for tobacco (pGSTTAK) and Zea mays (pZM/RMS-3) were constructed. All recombinant plasmids were identified by hybridisation probes, their integrity and orientation checked by restriction mapping and boundaries of completed vectors analysed by sequencing.

A variety of transient and stable transformation GUS vectors were constructed using approximately 3.8 Kb of the GST-II-27 promoter. Nde I was used to cut the GST-II-27 promoter at the ATG and 4 Kb upstream. This fragment was cut with EcoRI, blunted and cloned into Sma I site of pTAK (a Bin19 based promoterless GUS construct). The GST GUS cassette from pGSTTAK was then cloned into the transient assay vector pPUG (3.8 GST promoter and GUS). The same GST GUS cassette was also cloned into a pUC derived vector containing the Bar selectable cassette giving pZM/RMS-3.

Figure 8:
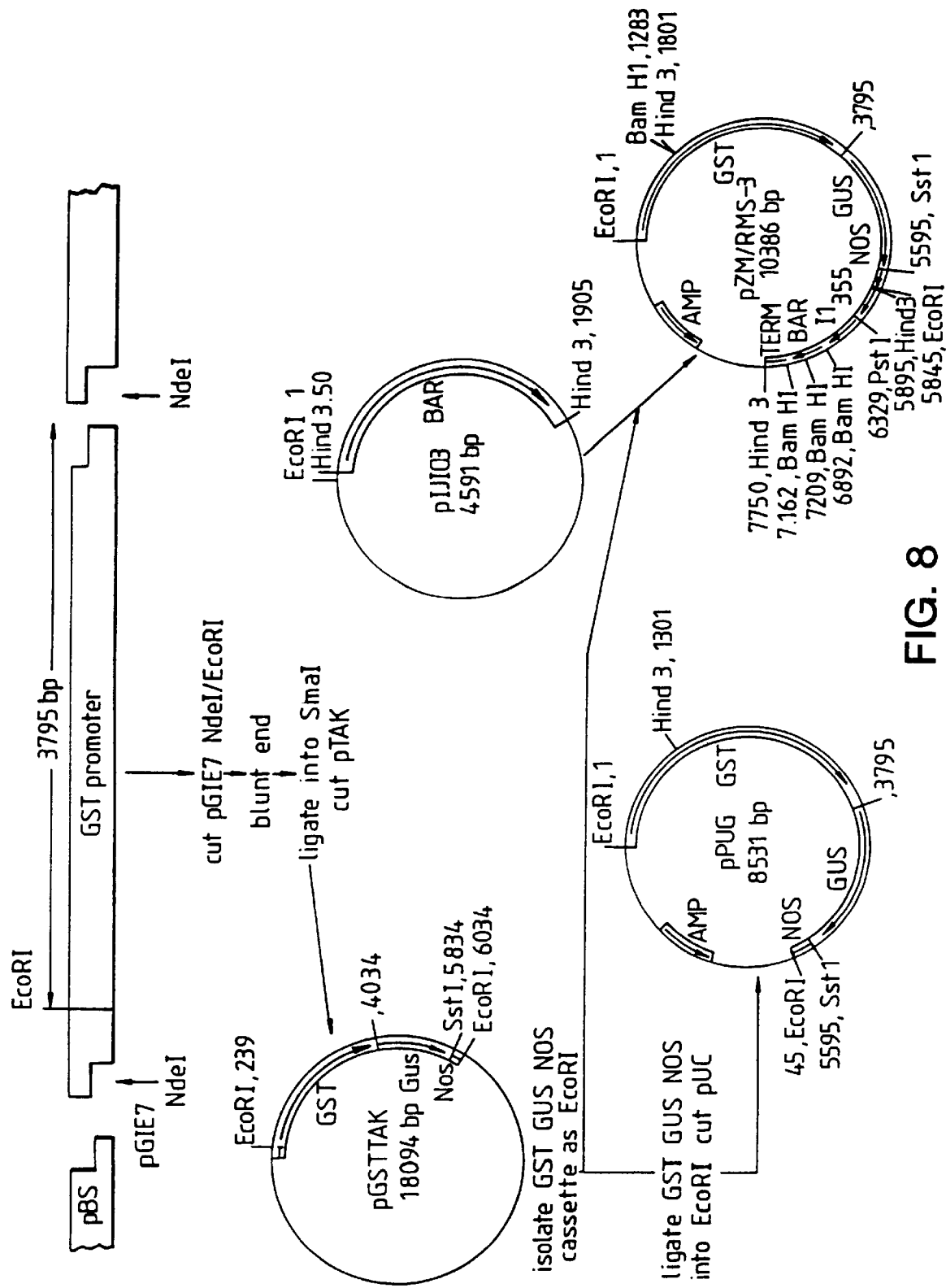
FIG. 8 gives an overview of GST GUS vector construction.
Figure 9:
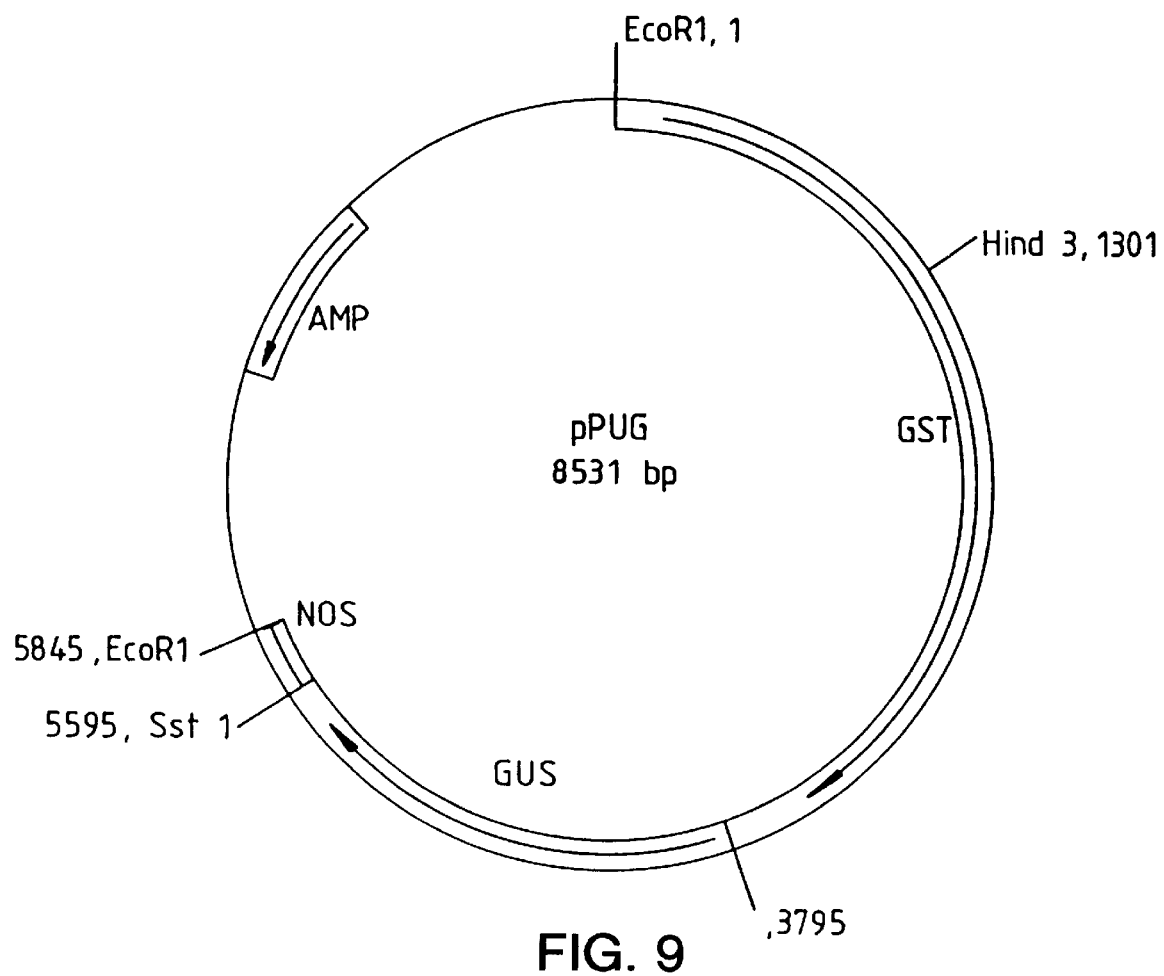
FIG. 9 shows the maize transient transformation vector, pPUG.
Figure 10:
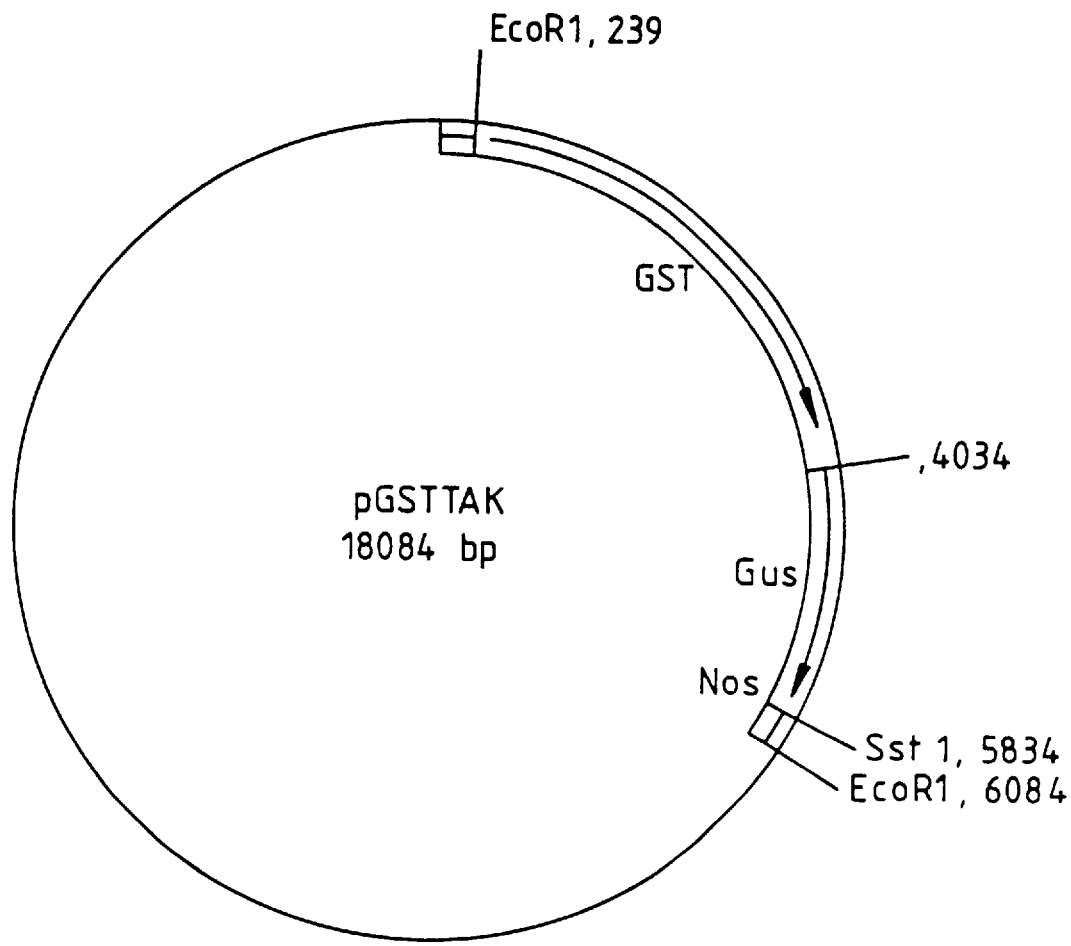
FIG. 10 shows the tobacco stable transformation vector, pGSTTAK.
Figure 11:
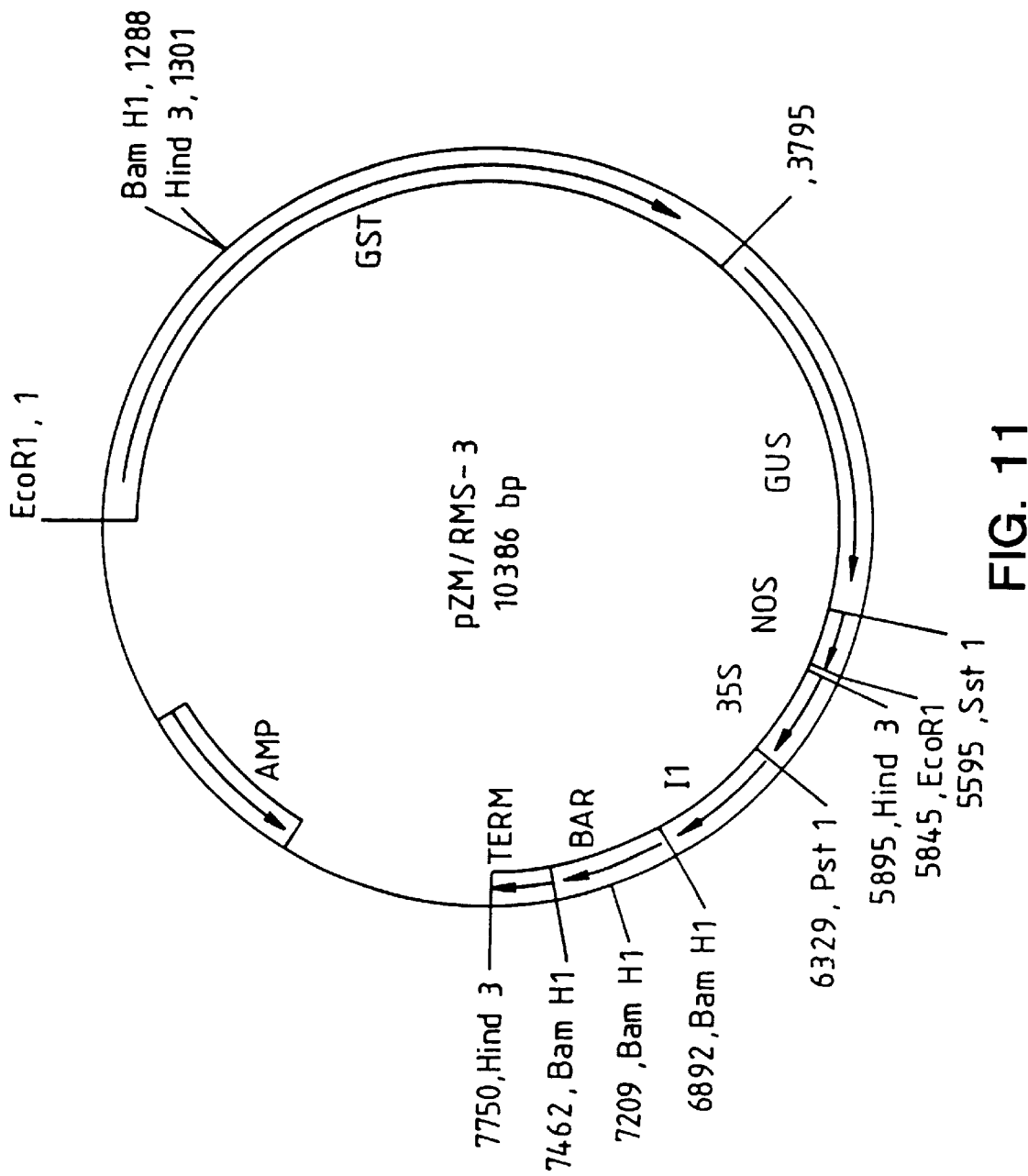
FIG. 11 shows the maize stable transformation vector, pZM/RMS-3.

FIG. 8 gives an overview of the method of vector construction. FIG. 9 shows the final structure of the maize transient transformation vector, pPUG; FIG. 10 shows the tobacco stable transformation vector, pGSTTAK; and FIG. 11 shows the maize stable transformation vector, pZM/RMS-3.

Protoplast Transient Expression Assay System

A series of protoplast transient assay experiments using pPUG were carried out to demonstrate the 3.8 kB GST-II-27 promoter region was transcriptionally active and that expression from this promoter could be induced by herbicide safeners.

Protoplasts were isolated form maize cell suspension lines or from in vitro grown maize leaves by a standard enzymatic digestion, sieving and washing procedure. Transformation was carried out by means of a modified PEG-mediated uptake method (based on Negrutiu et al, 1987, Plant Mol Biol, 8:363–373), using 25 $\mu$g DNA/0.4×10$^5$ protoplasts. Chemical was added to the protoplast culture medium at 3–300 ppm for induction of GST followed by incubation at 25° C. in the dark. Viability of the treated protoplasts was assessed after 24 hours prior to preparation of extracts. GUS expression was measured by means of a fluorimetric GUS assay (Jefferson, 1987, Plant Mol Biol Rep, 5:387–405).

Figure 12:
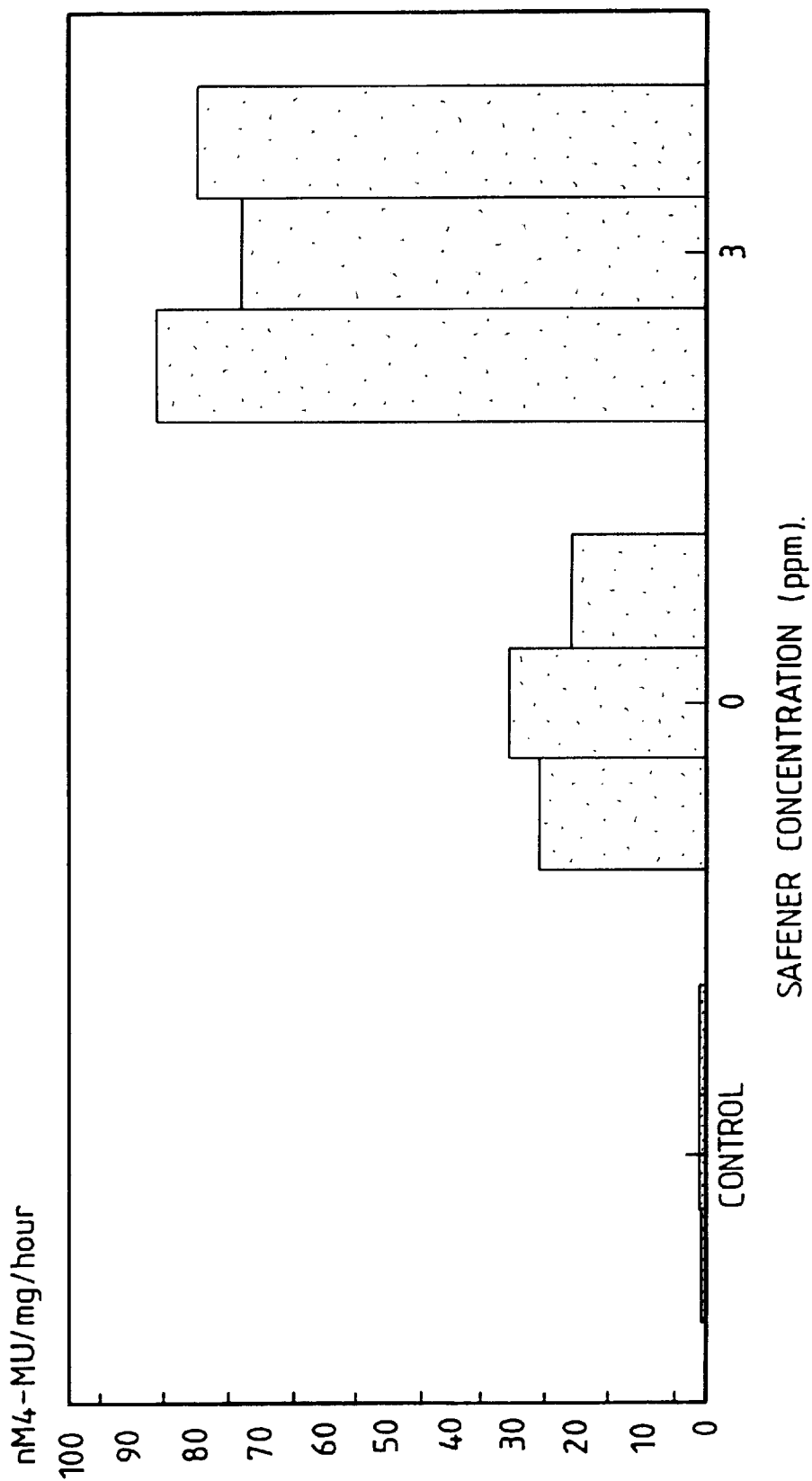
FIG. 12 shows results of the protoplast transient expression assays.

A summary of results is shown in FIG. 12 which gives the concentration of pPUG expression in protoplasts after 19 hours incubation with or without safener. Results demonstrate that the 3.8 Kb promoter of GST-II-27 is capable of controlling GUS levels in an inducible manner in a number of protoplast systems.

Stable Transformation Experiments in Tobacco

The Bin19 vector pGSTTAK containing 3.8 Kb of the GST-II-27 promoter 5' to the GUS reporter gene and nos terminator was used to generate transgenic tobacco using Agrobacterium Ti plasmid technology as described by Bevan (1984, Nucleic Acids Research, 12:8711–8721). Transformants produced by this procedure were used in leaf painting experiments in which 10 mg of formulated safener was applied to a 10 cm$^3$ region of leaf. A second application was made to the same area 48 hours later, and the tissue was harvested after a further 24 hours. Treated and untreated leaf tissue was assayed for GUS activity using the procedure of Jefferson (1987, Plant Mol Biol Rep, 5:387–405).

Figure 13:
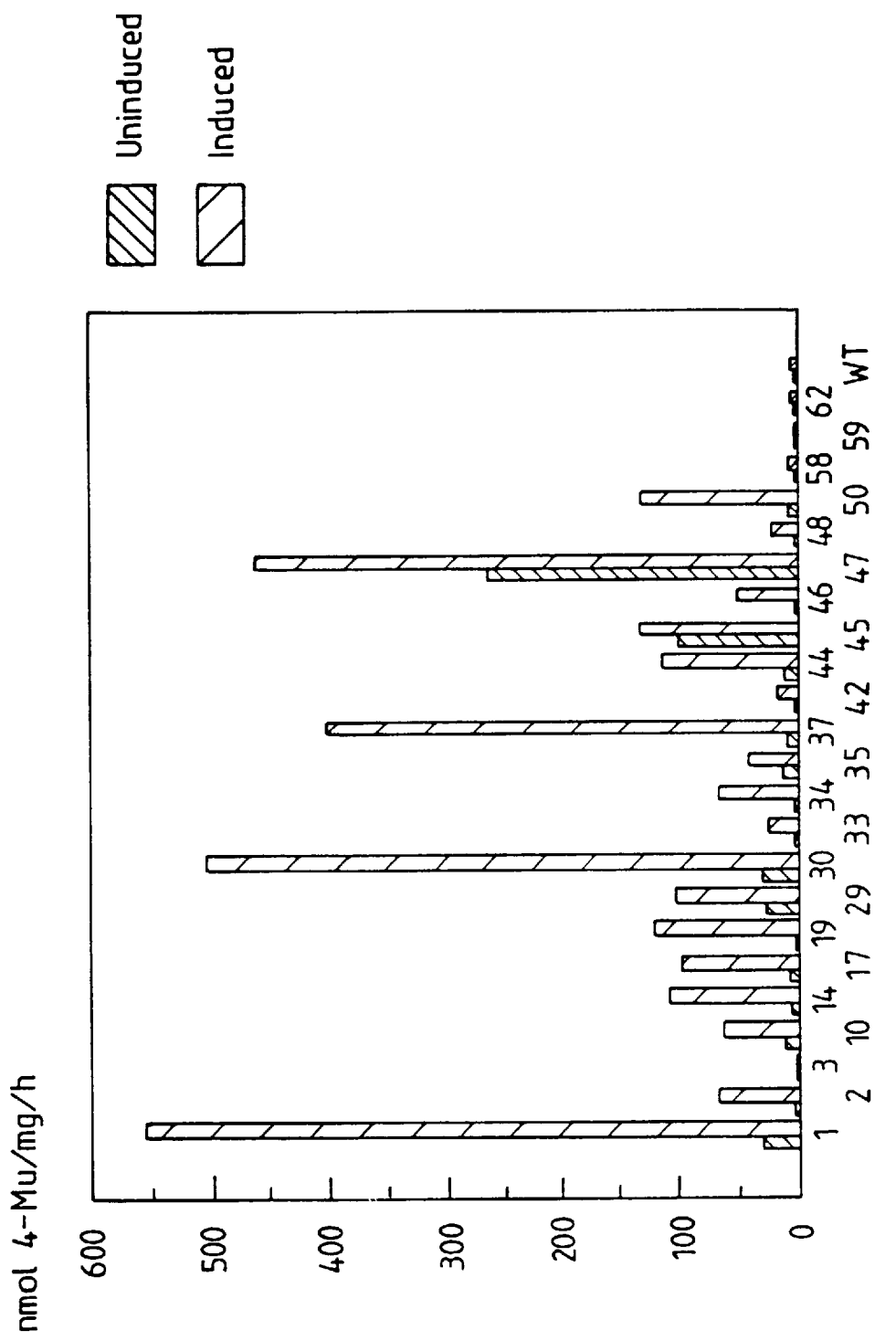
FIG. 13 shows results of the tobacco stable transformation experiments.

A range of transformants were examined using this method. As shown in FIG. 13, safener application had elevated GUS expression by 100 fold in some cases. This clearly demonstrates that the monocotyledonous GST-II-27 promoter can regulate gene expression in a dicotyledonous species in an inducible manner.

Stable Transformation Experiments in Maize

Figure 14:
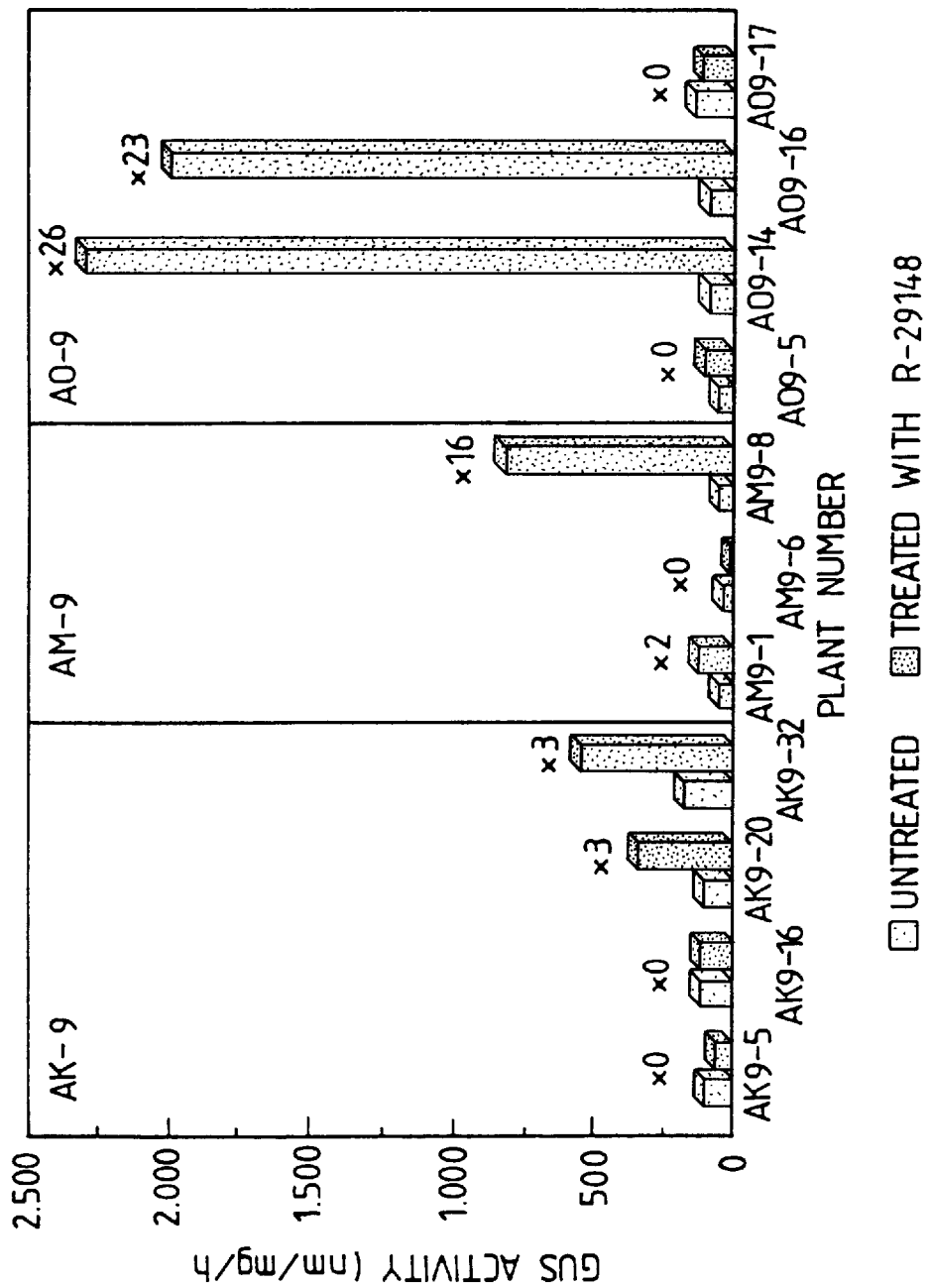
FIG. 14 shows results of the maize stable transformation experiments.

The GST GUS vector RMS 3 was used to generate transgenic maize plants using particle bombardment (Gordon-Kamm et al, 1990, Plant Cell, 2:603–618). When leaf tissue was painted with herbicide safener as described above, inducible GUS activity was observed (as shown in FIG. 14).

GST-II-27 Induction in Various Tissues

The induction of GST-II-27 in several tissues of developing maize was studied to determine how the promoter works in its natural environment.

Formulated R-29148 (2,2,5-trimethyl-3-(dichloroacetyl)-1,3-oxazolidine) or formulation alone were applied as a root drench to maize plants (400 mg R-29148/plant) and after a period of time crude protein extracts were prepared from samples of mature and immature leaf, root, stem and tassel. Western blot analysis was carried out using these extracts and the anti-GST-II-27-sera or the anti-GST-I-29-sera. The results show that the 29 kD subunit (GST-I-29) is constitutively expressed in all the tissues tested and was inducible in all tissues by safener application. The 27 kD subunit, specific to GST-II, was only constitutively expressed in root tissue. Subsequent to the root drench application of R-29148, GST-II expression was detected in all tissues tested. This induction was not detected in the plants treated with formulation lacking R-29148. Western blots showed tissue localisation of the GST-II 27 kD subunit in safener treated maize mature leaf, immature leaf, stem, root and tassel.

Results of these experiments suggest that the promoter of the invention may be used to control gene expression in a variety of transgenic tissues.

Field Trial Showing GST-II-27 Induction in Tassel Tissue by Safener Application A field trial was performed to examine the expression of GST isoforms in developing maize tassels subsequent to the external application of chemical safeners. The trial demonstrated the statistically significant induction of GST-II under field conditions.

Two safeners were used in the field trial: R-25788 (N,N-diallyl-2,2-dichloroacetamide) and R-29148 (2,2,5-trimethyl-3-(dichloroacetyl)-1,3-oxazolidine), and these were applied in a formulation of cyclohexanone, synperonic NPE1800 and Tween 85 or a formulation of Solvesso 100, Synperonic NB13 and Phenylsulphonate.

Safener was applied by a spray application using overhead spraying (30 cm above plants) at four application rates (three replications per rate) as follows:

X 2.58 Kg/Ha 2X 5.16 Kg/Ha 4X 10.32 Kg/Ha 8X 20.64 Kg/Ha).

The control treatments involved spraying formulation blanks 2F (treatment 2X without safener) and 8F (treatment 8X without safener).

After a period of time, the tassels were harvested and split into three sizes: pre-meiotic, meiotic and post-meiotic floret tissue. Crude protein extracts were prepared from floret tissue and stored at −70° C.

Western blot analysis was performed using these crude extracts and the antisera raised in sheep against the GST-I-29 or the GST-II-27 subunits. Antisheep antisera linked to Horseradish peroxidase was used as the secondary antisera and detection was achieved using Enhanced Chemical Luminescence (Amersham International PLC). The levels of GST-II-27 present in the crude extract was quantified by running standards of purified GST-II-27 in lanes of the SDS-PAGE gel adjacent to the crude extract samples and performing densitometric analysis on the blots.

The levels of GST-II induction was also determined by separating the GST isoforms by FPLC ion exchange chromatography and assaying for the presence of GST using CDNB as the substrate.

Figure 15:
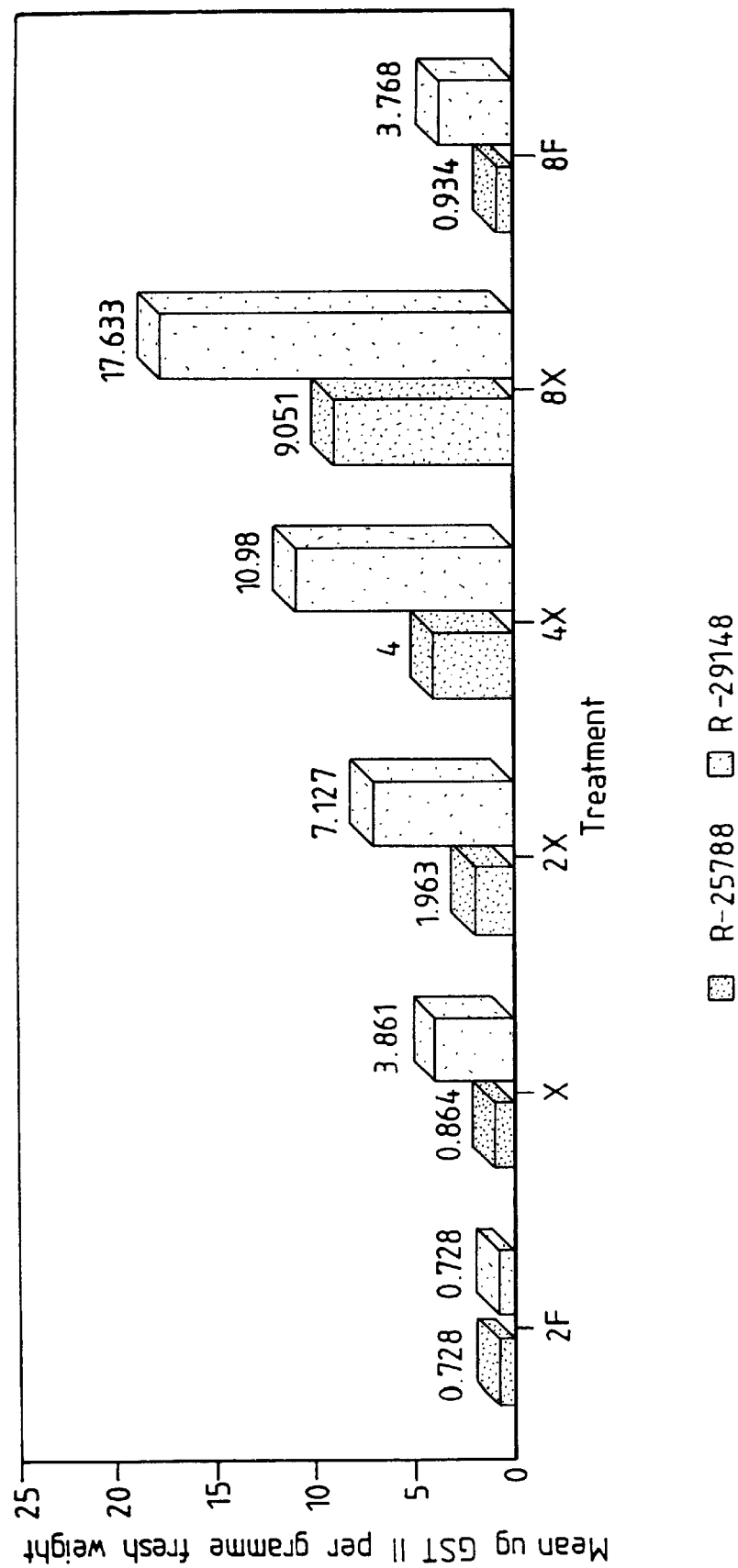
FIG. 15 shows GST II concentration following safener treatment of maize in field trials.
Figure 16:
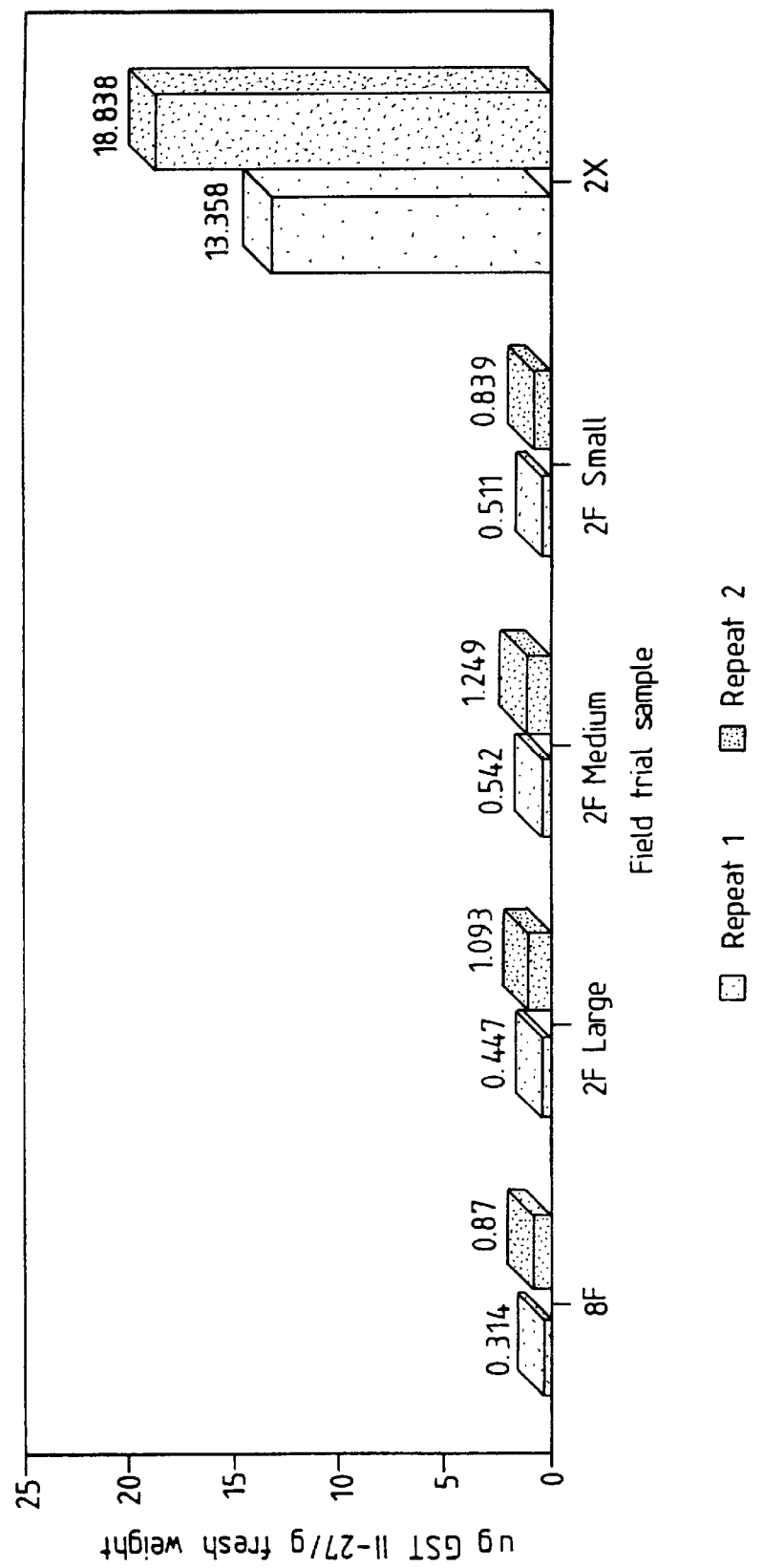
FIG. 16 shows GST II concentration in variously-sized uninduced maize tassels compared to induced tissue.

Some results of the field trials are given in FIGS. 15 and 16. FIG. 15 gives the overall mean values for treatment with R-25788 and R-29148. It is obvious that the presence of the inducing chemical (reatments X, 2X, 4X, 8X) causes an increase in the amount of the GST-II enzyme under field conditions when compared to the control plants (treatments 2F and 8F). FIG. 16 gives the amount of GST-II from 2F field trial tassel samples (large, medium and small), estimated by western analysis. When compared to the 2X treated samples, it is obvious that the presence of inducing chemical causes an increase in GST-II over the basal level.

These results show that the safeners R-29148 and R-25788 can be used to induce expression of GST-II under field conditions. These data, taken with the results from the studies with transgenic plants containing the GST-II-27 gene promoter, suggest that said promoter will provide a useful and efficient mechanism for controlling gene expression in transgenic plants under field conditions.

Production of Herbicide Resistant Transgenic Plants Expressing the GST-II Enzyme The nucleotide sequence of a cDNA encoding GST-I-29 was published by Wiegand et al. in Plant Mol Biol, 1986, 7:235–243. Using this sequence, a specific oligonucleotide probe was designed and used to isolate a full length cDNA (plasmid pIJ4) encoding GST-I-29 from a safener induced seedling root cDNA library. Isolation of the cDNA encoding GST-II-27 (as shown in FIGS. 2A–2C) has already been described. The full length cDNAs may be incorporated into Bin19-based vectors under the control of the 35S CaMV promoter.

Figure 17:
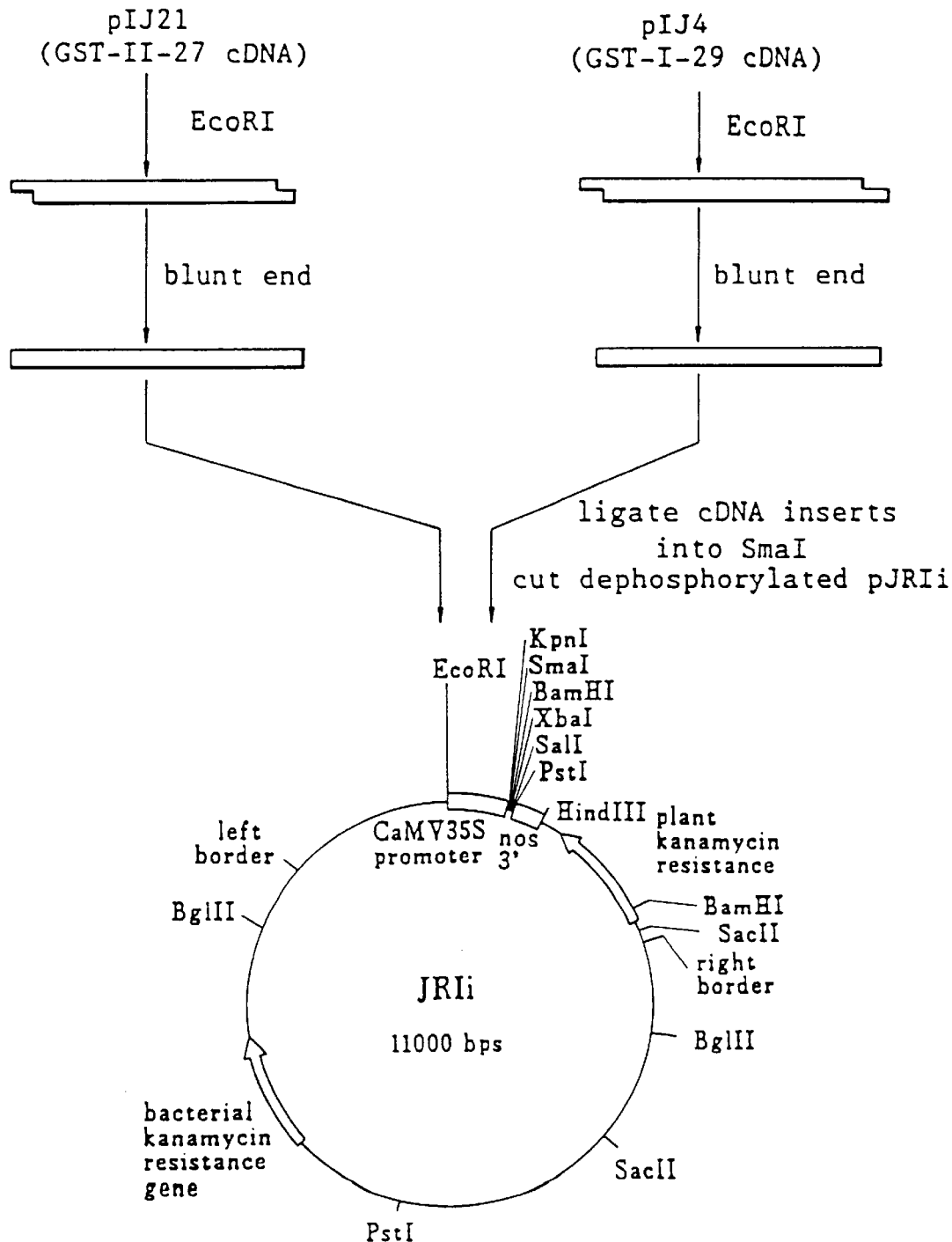
FIG. 17 illustrates preparation of the vectors containing the CaMV35S-GST-I-29 or CaMV35S-GST-II-27 cassette.

FIG. 17 shows how these constructs may be prepared. The full length GST-I-29 coding region and the full length GST-II-27 sequence are isolated from pIJ4 and from pIJ21 respectively by digestion with EcoRI. These fragments are filled in using Klenow/T4 polymerase to produce blunt ends. The blunt-ended fragments are then ligated 3' to the 35S CaMV promoter of pJRIi at the SmaI cloning site. Recombinants containing cDNA inserts in the correct orientation are be selected using restriction mapping analysis.

Tobacco plants may be transformed with vectors containing either the CaMV35S-GST-I-29 or the CaMV35S-GST-II-27 cassette using the protocols already described. Transformants expressing the respective GST-II subunits (29 kD or 27 kD) may be determined by Western blotting analysis with subunit specific antisera (as already described). Such transformants may be crossed to produce progeny expressing both GST-I-29 and GST-II-27, resulting in a herbicide resistant phenotype.

We claim:

1. A cDNA sequence encoding glutathione-S transferase, isoform II, 27 kD subunit having the amino acid sequence identified in SEQ ID NO:2.

2. The cDNA sequence as claimed in claim 1 having the nucleotide sequence identified in SEQ ID NO:1.

3. A cDNA sequence encoding glutathione-S transferase, isoform II, 27 kD subunit having the amino acid sequence identified in SEQ ID NO:2 and having the nucleotide sequence identified in SEQ ID NO:1.

4. A method to produce a herbicide resistant transgenic plant which comprises the incorporation of DNA encoding the GST-II 27 kD subunit having the amino acid sequence identified in SEQ ID NO:2 into the plant such that a glutathione-S-transferase enzyme is expressed.

5. The method as claimed in claim 4 further comprising the incorporation of DNA encoding the GST-I 29 kD subunit into the plant.

6. The method as claimed in claim 4 wherein DNA encoding GST-II 27 kD subunit is introduced into a first plant and DNA encoding the GST-I 29 kD subunit is introduced into a second plant, and the first and second plant are crossed to produce herbicide resistant progeny.

7. The method as claimed in claim 4 further comprising the incorporation of DNA encoding the GST-III 26 kD subunit into the plant.

8. The method as claimed in claim 7 further comprising the incorporation of DNA encoding the GST-I 29 kD subunit into the plant.

9. The method as claimed in any one of claims 4 to 8 in which the DNA encoding the GST polypeptide is under the control of a constitutive promoter.

10. A method as claimed in claim 4 in which the DNA encoding the GST polypeptide is under the control of an inducible promoter.

11. A method as claimed in claim 10 in which the inducible promoter is the GST-II-27 promoter.

12. A herbicide resistant transgenic plant produced by the method as claimed in claim 11.

13. A plant as claimed in claim 12 in which herbicide resistance is constitutive.

14. A plant as claimed in claim 13 which is maize.

15. A plant as claimed in claim 12 in which herbicide resistance is inducible.

16. The progeny or the seeds of the herbicide resistant transgenic plant as claimed in claim 12.

17. A method of selectively controlling weeds in a field of transgenic plants produced according to the method of claim 4, comprising applying to the transgenic plants and weeds in the field an effective amount of a herbicide to control the weeds without significantly affecting the transgenic plants.

* * * * *